(12) United States Patent
Jaynes

(10) Patent No.: US 9,487,560 B2
(45) Date of Patent: Nov. 8, 2016

(54) ANGIOGENIC ACTIVE LYTIC PEPTIDES

(71) Applicant: Jesse Michael Jaynes, Auburn, AL (US)

(72) Inventor: Jesse Michael Jaynes, Auburn, AL (US)

(73) Assignee: ISSAR Pharmaceuticals Ltd, Hyderabad (IN)

( * ) Notice: Subject to any disclaimer, the term of this patent is extended or adjusted under 35 U.S.C. 154(b) by 63 days.

(21) Appl. No.: 13/986,434

(22) Filed: May 2, 2013

(65) Prior Publication Data
US 2014/0329753 A1    Nov. 6, 2014

(51) Int. Cl.
*A61K 38/04* (2006.01)
*C07K 7/08* (2006.01)
*C07K 7/06* (2006.01)

(52) U.S. Cl.
CPC .. *C07K 7/08* (2013.01); *C07K 7/06* (2013.01)

(58) Field of Classification Search
CPC ................................. C07K 7/08; C07K 7/06
See application file for complete search history.

(56) References Cited

U.S. PATENT DOCUMENTS 5,955,573 A * 9/1999 Garbarino ............. A61K 38/10
530/324
2005/0187151 A1* 8/2005 Strom ................ C07K 14/4723
514/2.4

* cited by examiner

*Primary Examiner* — Julie Ha
*Assistant Examiner* — Li Ni Komatsu
(74) *Attorney, Agent, or Firm* — John Dodds

(57) ABSTRACT

This invention relates to novel synthetic lytic peptide fragments of full-length peptides with the capacity to modulate angiogenic activity in mammals. The invention also relates to the use of such peptides in pharmaceutical compositions and in methods for treating diseases or disorders that are associated with angiogenic activity.

4 Claims, 23 Drawing Sheets

| AA | Vol. | D | Hyd. | Hyd. % | Lum. |
|---|---|---|---|---|---|
| F | 189.9 | 7.13 | 3.7 | 100 | 128 |
| M | 162.9 | 6.78 | 3.4 | 92 | 138 |
| I | 166.7 | 6.83 | 3.1 | 84 | 149 |
| L | 166.7 | 6.83 | 2.8 | 76 | 159 |
| V | 140.0 | 6.44 | 2.6 | 70 | 166 |
| C | 108.5 | 5.92 | 2.0 | 54 | 187 |
| W | 227.8 | 7.58 | 1.9 | 51 | 190 |
| A | 88.6 | 5.53 | 1.6 | 43 | 201 |
| T | 116.1 | 6.05 | 1.2 | 32 | 214 |
| G | 60.1 | 4.86 | 1.0 | 27 | 221 |
| S | 89.0 | 5.54 | 0.6 | 16 | 235 |
| P | 122.7 | 6.16 | -0.2 | 2 | 254 |
| Y | 193.6 | 7.18 | -0.7 | 6 | 249 |
| H | 153.2 | 6.64 | -3.0 | 25 | 225 |
| Q | 143.9 | 6.50 | -4.1 | 34 | 213 |
| N | 117.7 | 6.08 | -4.8 | 39 | 206 |
| E | 138.4 | 6.42 | -8.2 | 67 | 170 |
| K | 168.6 | 6.85 | -8.8 | 72 | 164 |
| D | 111.1 | 5.96 | -9.2 | 75 | 159 |
| R | 173.4 | 6.92 | -12.2 | 100 | 128 |

Fig. 2.

pMim classes 1, 2 and 3 are alpha-helical and 4, 5 and 6 are beta sheets

Class 1

Melittin         GIGAVLKVLTTGLPALISWIKRKRQQ    (SEQ ID NO: 9)

Pipinin 1        FLPIIAGVAAKVLPKIFCAISKKC      (SEQ ID NO: 10)

JC1A21           FAFAFKAFKKAFKKFKKAFKKAF       (SEQ ID NO: 15)

Class 2

Adenoregulin  GLWSKIKEVGKEAAKAAAKAAGKAALGAVSEAV  (SEQ ID NO: 11)

Cecropin B    KWKVFKKIEKMGRNIRNGIVKAGPAIAVLGEAKAL  (SEQ ID NO: 12)

JC15          FAKKFAKKFKKFAKKFAKFAFAF      (SEQ ID NO: 5)

Class 3

Andropin      VFIDILDKVENAIHNAAQVGIGFAKPFEKLINPK   (SEQ ID NO: 13)
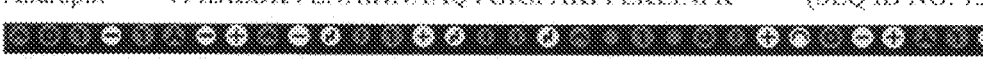

Magainin 2    GIGKFLHSAKKFGKAFVGEIMNS     (SEQ ID NO: 14)

JC3M1         FVKKVAKKAKKVAKKAVKVAKKV     (SEQ ID NO: 16)

Figure 5 b-Defensin 1   DFASCHTNGGICLPNRCPGHMIQIGICFRPRVKCCRSW (SEQ ID NO:17)
Protegrin   RGGRLCYCRRRFCVCVGR (SEQ ID NO:19)
JC41   FKLRAKIKVRLRAKIKL (SEQ ID NO:18)
Fig. 6

Human Plasminogen (Sequence ID No: 20)

MEHKEVVLLLLLFLKSGQGEPLDDYVNTQGASLFSVTKKQLGAGSIEECAAKCE
EDEEFTCRAFQYHSKEQQCVIMAENRKSSIIRMRDVVLFEKKVYLSECKTGNGK
NYRGTMSKTKNGITCQKWSSTSPHRPRFSPATHPSEGLEENYCRNPDNDPQGPW
CYTTDPEKRYDYCDILECEEECMHCSGENYDGKISKIMSGLECQAWDSQSPHA
HGYIPSKFPNKNLKKNYCRNPDRELRPWCFTTDPNKRWELCDIPRCTTPPPSSG
PTYQCLKGTGENYRGNVAVTVSGHTCQHWSAQTPHTHNRTPENFPCKNLDENY
CRNPDGKRAPWCHTTNSQVRWEYCKIPSCDSSPVSTEQLAPTAPPELTPVVQDC
YHGDGQSYRGTSSTTTTGKKCQSWSSMTPHRHQKTPENYPNAGLTMNYCRNPD
ADKGPWCFTTDPSVRWEYCNLKKCSGTEASVVAPPPVVLLPDVETPSEEDCMF
GNGKGYRGKRATTVTGTPCQDWAAQEPHRHSIFTPETNPRAGLEKNYCRNPD
GDVGGPWCYTTNPRKLYDYCDVPQCAAPSFDCGKPQVEPKKCPGRVVGGCVA
HPHSWPWQVSLRTRFGMHFCGGTLISPEWVLTAAHCLEKSPRPSSYKVILGAHQ
EVNLEPHVQEIEVSRLFLEPTRKDIALLKLSSPAVITDKVIPACLPSPNYVVADRTE
CFITGWGETQGTFGAGLLKEAQLPVIENKVCNRYEFLNGRVQSTELCAGHLAGG
TDSCQGDSGGPLVCFEKDKYILQGVTSWGLGCARPNKPGVYVRVSRFVTWIEGV
MRNN

Fig. 7

PL-1        QAWDSQSPHAHGYIPSKFPNKNLKKNY (SEQ ID NO: 22)
PL-2        MFGNGKGYRGKRATTVTGTP (SEQ ID NO: 3)
Fig. 8

Fragment of Human Collagen XVIII (SEQ ID #: 23)
GEVGADGIPGFPGLPGREGIAGPQGPKGDRGSRGEKGDPGKDGLGQPGLP
GPRGPPGPVVYVSEQDGSVLSVPQPEGRRGPAGFPGPAGPKGNLGSKGE
LGSPGPKGEKGEPGSIFSPDGGALGPAQKGAKGEPGFRGPPGLYGRPGYK
GEIGFPGRPGRPGMNGLKGEKGEPGDASLGFGMRGMPGPPGPPGPPGPPG
TPVYDSNVFAESSRPGPPGLPGNQGPPGPKGPKGEVGPPGPPGQFPFDFLQ
KEAEMKGEKGDRGDAGQKGERGEPGGGGFFGSSLPGAPGAPGPRGYPGIP
GPKGESIRGQPGPPGPQGPPGIGYEGRQGPPGPPGPPGPPSFPGPHRQTISVPG
PPGPPGPPGPPGTMGASSGQVRLWATRQAMLGQVHEVPEGWLIFVAEQ
EELYVRVQNGFRKVQLEARTPLPRGTDNEVAALQPPVVQLHDSNPYPRR
EHPHPTARPWRADDILASPPGLPEPQPYPGGPHHSSYVHCGPARPTSPPA
HSHRDFQPVLHLVALNSPLSGGMRGIRGADFQCFQQARAVGLAGTFRAF
LSSRLQDLYSIVRRADRAAVPIVNLKDELLFPSWEALFSGSEGPLKPGAR
IFSFDGKDVLRHPTWPQKSVWHGSDPNGRRLTESYCETWRTEAPSATGQA
SSLLGQRLLGQSAASCHHAYIVLCIENSFMTASK

Fig. 9

C-1        IVRRADRAAVPIVNLKDELL (SEQ ID NO: 24)

Platelet Factor 4 (SEQ ID NO: 25)

EAEEDGDLQCLCVKTTSQVRPRHITSLEVIKAGPHCPTAQLIATLKNGRKICLDLQAPLYKKIIKKLLES

Fig. 11

PF-1    PTAQLIATLKNGRKI (SEQ ID NO: 26)
PF-2    LDLQAPLYKKIIKKLLES (SEQ ID NO: 27)
Fig. 12

Matrigel

Fig. 15

IL8 (CXCL8) (SEQ ID NO: 57)
MTSKLAVALLAAFLISAALCEGAVLPRSAKELRCQCIKTYSKPFHPK
FIKELRVIESGPHCANTEIIVKLSDGRELCLDPKENWVQRVVEKFLKR
AENS

MIG (CXCL9) (SEQ ID NO: 31)
MKKSGVLFLLGIILLVLIGVQGTPVVRKGRCSCISTNQGTIHLQSLKD
LKQFAPSPSCEKIEIIATLKNGVQTCLNPDSADVKELIKKWEKQVSQK
KKQKNGKKHQKKKVLKVRKSQRSRQKKTT

MCP1 (CCL2) (SEQ ID NO: 32)
MKVSAALLCLLLIAATFIPQGLAQPDAINAPVTCCYNFTNRKISVQRL
ASYRRITSSKCPKEAVIFKTIVAKEICADPKQKWVQDSMDHLDKQTQ
TPKT

MIP-1a (CCL3) (SEQ ID NO: 33)
MQVSTAALAVLLCTMALCNQFSASLAADTPTACCFSYTSRQIPQNFI
ADYFETSSQCSKPGVIFLTKRSRQVCADPSEEWVQKYVSDLELSA

RANTES (CCL5) (SEQ ID NO: 34)
MKVSAAALAVILIATALCAPASASPYSSDTTPCCFAYIARPLPRAHIK
EYFYTSGKCSNPAVVFVTRKNRQVCANPEKKWVREYINSLEMS

Fig. 17

| Fragment | # |
|---|---|
| 10N (Sequence ID# 1) | A |
| CCL19-f (Sequence ID# 45) | B |
| XCL2-f (Sequence ID# 49) | C |
| CX3CL1-f (Sequence ID# 50) | D |
| CXCL4-f (Sequence ID# 53) | E |
| CXCL5-f (Sequence ID# 54) | F |
| CXCL8-f (Sequence ID# 57) | G |
| CXCL10-f (Sequence ID# 58) | H |
| IL10-f (Sequence ID# 60) | I |
| IL24-f (Sequence ID# 66) | J |
| Endostatin-f (Sequence ID# 69) | K |

Figure 19A

ANGIOGENIC ACTIVE LYTIC PEPTIDES

This application is a Continuation-in-Part of Pending application Ser. No. 13/135,978 and claims priority under 35 U.S.C 119 (e) of U.S. Provisional Application 61/400,822

FIELD OF THE INVENTION

This invention relates to novel synthetic lytic peptide fragments of full-length peptides having the capacity to modulate angiogenic activity in mammals. The invention also relates to the use of such peptide fragments in pharmaceutical compositions and to methods for treating diseases or disorders that are associated with angiogenic activity.

BACKGROUND OF THE INVENTION

Angiogenesis is a physiological process in which new blood vessels grow from pre-existing ones. This growth may be spontaneous formation of blood vessels or alternatively by the splitting of new blood vessels from existing ones.

Angiogenesis is a normal process in growth and development and in wound healing. It may play a key role in various healing processes among mammals. Among the various growth factors that influence angiogenesis naturally occurring vascular endothelial growth factor (VEGF) is known to be a major contributor by increasing the number of capillaries in a given network. VEGF is a signal protein produced by cells that stimulates angiogenesis. It is part of the system that restores the oxygen supply to tissues when blood circulation is inadequate. VEGF's normal function is to create new blood vessels during embryonic development, new blood vessels after injury, muscles following exercise, and new vessels to bypass blocked vessels The process of angiogenesis may be a target for fighting diseases that are characterized by either under development of blood vessels or overdevelopment. The presence of blood vessels, where there should be none may affect the properties of a tissue and may cause for example, disease or failure. Alternatively, the absence of blood vessels may inhibit repair or essential functions of a particular tissue. Several diseases such as ischemic chronic wounds are the result of failure or insufficient blood vessel formation and may be treated by a local expansion of blood vessels. Other diseases, such as age-related macular degeneration may be stimulated by expansion of blood vessels in the eye, interfering with normal eye functions.

In 1971, J. Folkman published in the New England Journal of Medicine, a hypothesis that tumor growth is angiogenesis dependent. Folkman introduced the concept that tumor is probably secrete diffusable molecules that could stimulate the growth of new blood vessels toward the tumor and that the resulting tumor blood vessel growth could conceivably be prevented or interrupted by angiogenesis inhibitors Tumor angiogenesis is the proliferation of a network of blood vessels that penetrates into cancerous growths supplying nutrients and oxygen while removing waste. The process actually starts with cancerous tumor cells releasing molecules that signal surrounding host tissue, thus activating the release of certain proteins, which encourage growth of new blood vessels. Angiogenesis inhibitors are drugs that block the development of new blood vessels, and. By blocking the development of new blood vessels. Researchers hope to cut off the tumor supply of oxygen and nutrients, which in turn might stop the tumor from growing and spreading to other parts of the body.

In the 1980s, the pharmaceutical industry applied these concepts in the treatment of disease by creating new therapeutic compounds for modulating new blood vessel in tumor growth. In 2004 Avastin (bevacizumab), a humanized anti-VEGF monoclonal antibody was the first angiogenesis inhibitor approved by the Food and Drug Administration for the treatment of colorectal cancer. It has been estimated that over 20,000 cancer patients worldwide have received experimental forms of anti-angiogenic therapy.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

A decade of clinical testing, both gene and protein-based therapies designed to stimulate angiogenesis in under perfused tissues and organs has resulted in disappointing results; however, results from more recent studies with redesigned clinical protocols have given new hope that angiogenesis therapy will become a preferred treatment for sufferers of cardiovascular disease resulting from occluded or stenotic vessels.

SUMMARY OF THE INVENTION

Because the modulation of angiogenesis has been shown to be a significant causative factor in the control of certain disorders and diseases, it is necessary to find agents which are safe and efficacious in either inhibiting or stimulating angiogenesis.

Additional features and advantages of the present invention will be set forth in part and in a description which follows, and in part will be apparent from the description, or may be learned by practice of the present invention. The objectives and advantages of the invention will be realized and attained by means of the elements, combinations, composition, and process particularly pointed out in the written description and appended claims.

To achieve the objects and in accordance with the purpose of the present invention, as embodied and broadly described herein, the present invention relates to new and novel synthetic lytic peptides which effectively enhance or inhibit angiogenesis and are therefore effective therapeutic agents in the treatment of disease in mammals.

In one aspect the present invention relates to synthetic lytic peptides having angiogenesis activity which are in the physical form of molecular fragments derived from corresponding full-length protein molecules. More particularly, this invention relates to peptide fragments that inhibit angiogenesis and are selected from peptide sequence: FAKKFAKKFK (SEQ ID NO: 1), IVRRADRAAVPIVNLKDELL (SEQ ID NO: 2) or MFGNGKGYRGKRATTVTGTP (SEQ ID NO: 3).

In another embodiment of the present invention, a peptide fragment is provided having anti-inflammatory activity bearing the peptide sequence FAKKFAKKFK (SEQ ID NO: 1).

In another aspect, the present invention provides a method for treating chronic inflammation comprising administering to a mammal in need of such treatment a peptide fragment bearing the peptide sequence FAKKFAKKFK (SEQ ID NO: 1).

In yet another embodiment, the present invention provides a method for treating chronic inflammation related disorders or conditions selected from among arthritis, ulcerated colitis, Crohn's disease, cancer, multiple sclerosis, cervical spondylosis, tinnitus, systemic lupus, erythematosis, graft rejection, psoriasis, arteriosclerosis, hypertension and ischemia-reperfusion comprising administering to a mammal in need of such treatment a peptide fragment bearing the peptide sequence FAKKFAKKFK (SEQ ID NO: 1), wherein said fragment FAKKFAKKFK is derived from peptide FAKKFAKKFKKFAKKFAKFAFAF (SEQ ID No.5).

In another aspect, the present invention provides a pharmaceutical composition for the treatment of disorders or diseases which are ameliorated by the inhibition of angiogenisis comprising a peptide fragment having the sequence FAKKFAKKFK (SEQ ID NO: 1), IVRRADRAAVPIVNLKDELL (SEQ ID NO: 2), MFGNGKGYRGKRATTVTGTP (SEQ ID NO: 3) or combinations thereof.

In another embodiment of the present invention, a peptide fragment is provided according to claim 1, having the capacity to accelerate angiogenesis wherein said peptide fragment has the sequence FAKKFAKKFKKFAKFAFAF (SEQ ID NO: 4), FAKKFAKKFAKKFAK (SEQ ID NO: 6), KKFKKFAKKFAKFAF (SEQ ID NO: 7) or FAKKFAKKFKKF (SEQ ID NO: 8) or a pharmaceutically acceptable salt thereof.

In another aspect, the present invention provides a pharmaceutical composition for the treatment of disorders or diseases which are ameliorated by the acceleration of angiogenesis comprising treatment of a mammal with an effective amount of a peptide fragment having the sequence FAKKFAKKFKKFAKFAFAF (SEQ ID NO: 4), FAKKFAKKFAKKFAK (SEQ ID NO: 6), KKFKKFAKKFAKFAF (SEQ ID NO: 7) or FAKKFAKKFKKF (SEQ ID NO: 8) or a pharmaceutically acceptable salt thereof.

In another aspect, the present invention provides a method for treating ulcerative colitis in a mammal comprising administering to said mammal in need of such treatment an effective amount of the peptide as defined in claim 2 or a pharmaceutically acceptable salt thereof.

In another embodiment of the present invention, a peptide fragment is provided according to claim 2, having the capacity to modulate inflammatory bowel disease and ulcerative colitis in a mammal.

BRIEF DESCRIPTION OF THE DRAWINGS

FIG. 2 provides physical characteristic of the 20 essential amino acids. The total volume, in cubic angstroms, is derived from the van der Waals' radii occupied by the amino acid when it is in a protein. D is the diameter of the amino acid. Hydrophobicity is in kcal/mol and is the amount of energy necessary to place the amino acid, when in an alpha-helical protein, from the membrane interior to its exterior.

FIG. 5 shows sequences of natural lytic peptides melittin (SEQ ID NO: 9), Pipinin1 (SEQ ID NO: 10), adenoregulin (SEQ ID NO: 11), cecropin B (SEQ ID NO:12), adropin (SEQ ID NO:13), magainin 2 (SEQ ID NO: 14) and their optimized analogs JC15 (SEQ ID NO: 5) and JC3M1 (SEQ ID NO:16)

FIG. 6 shows sequences of a defensin (SEQ ID NO:17) and a protegrin (SEQ ID NO: 19) along with an optimized analog JC41 (SEQ ID NO:18).

FIG. 7 shows the sequence of Human Plasminogen protein (SEQ ID NO: 20) including the sequence of angiostatin protein (SEQ ID NO: 21) derived from it (underlined sequence). PL 1 (SEQ ID NO: 22) and PL 2 (SEQ ID NO: 3) are also shown with shadowing.

FIG. 8 shows sequences of fragments PL-1 (SEQ ID NO: 22) and PL-2 (SEQ ID NO: 3) derived from Human plasminogen protein FIG. 9 shows the sequence of a fragment of Human Collagen XVIII (SEQ ID NO: 23). The underlined part of the sequence is the sequence of endostatin (SEQ ID NO: 70). Fragment C-1 (SEQ ID NO: 24) is shown with shadowing.

FIG. 11 shows the sequence of platelet factor-4 (SEQ ID NO: 25). Shadowed sequences represent PF1 (SEQ ID NO: 26) and PF2 (SEQ ID NO: 27).

FIG. 12 shows sequences of fragments PF-1 (SEQ ID NO: 26) and PF-2 (SEQ ID NO: 27) derived form Platelet Factor 4

FIG. 15 shows the sequences of natural and synthetic peptides of Example The following sequences are shown: JC15 (SEQ ID NO: 5), JC15-18 (SEQ ID NO: 28), JC15-15C (SEQ ID NO: 7), JC15-10C (SEQ ID NO: 29), JC15-12N (SEQ ID NO: 8), JC15-10N (SEQ ID NO: 1) C-1 (SEQ ID NO: 24), PF-2 (SEQ ID NO: 27), PF-1 (SEQ ID NO: 26), PL-1 (SEQ ID NO: 22), PL-2 (SEQ ID NO: 3).

FIG. 17 shows the amino acid sequences of the chemokines of Table 7 Following chemokine sequences are shown: IL8 (SEQ ID NO: 31), MIG (SEQ ID NO: 32), MCP1 (SEQ ID NO: 34), MIP-1a (SEQ ID NO: 35), RANTES (SEQ ID NO: 36).

FIG. 19A is a display of selected fragments from several cytokines and endostatin (derivation on the left, designation on the right) compared to 10N of JC15. The boxes indicate those amino acids out of place in terms of hydrophobicity/hydrophilicity.

TABLES

TABLE 1

Figure 1:
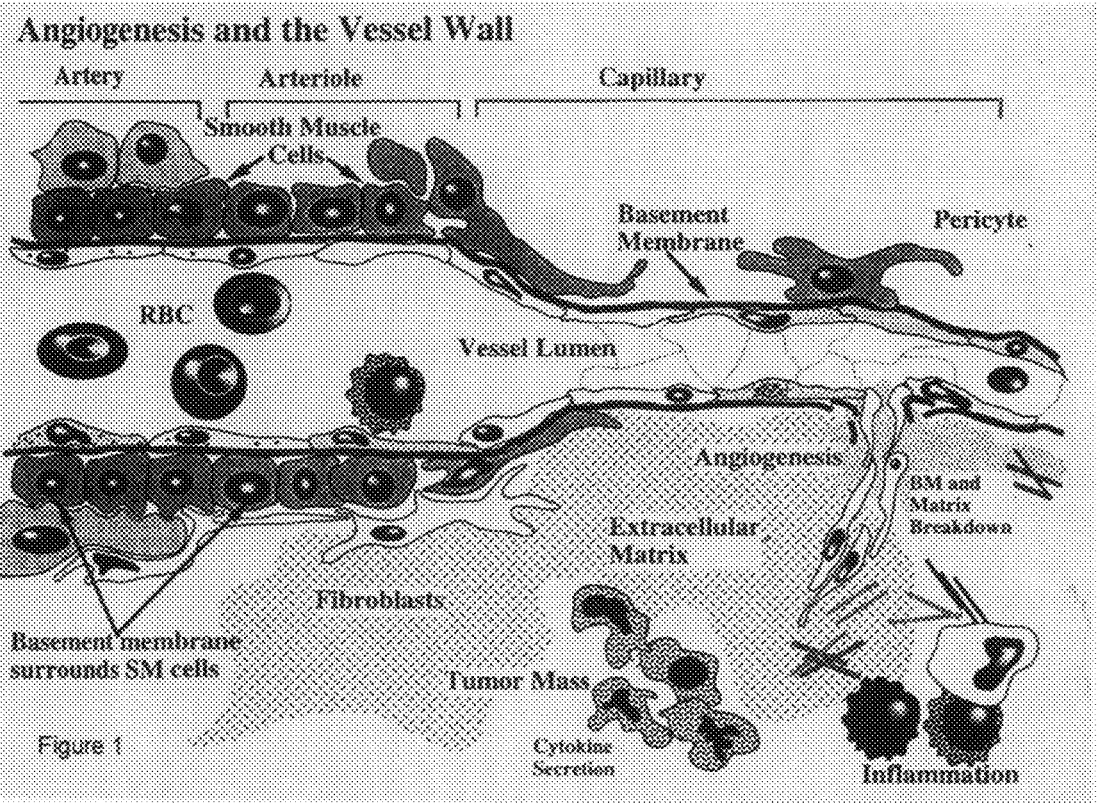
FIG. 1 illustrates the angiogenic process.
Figure 3:
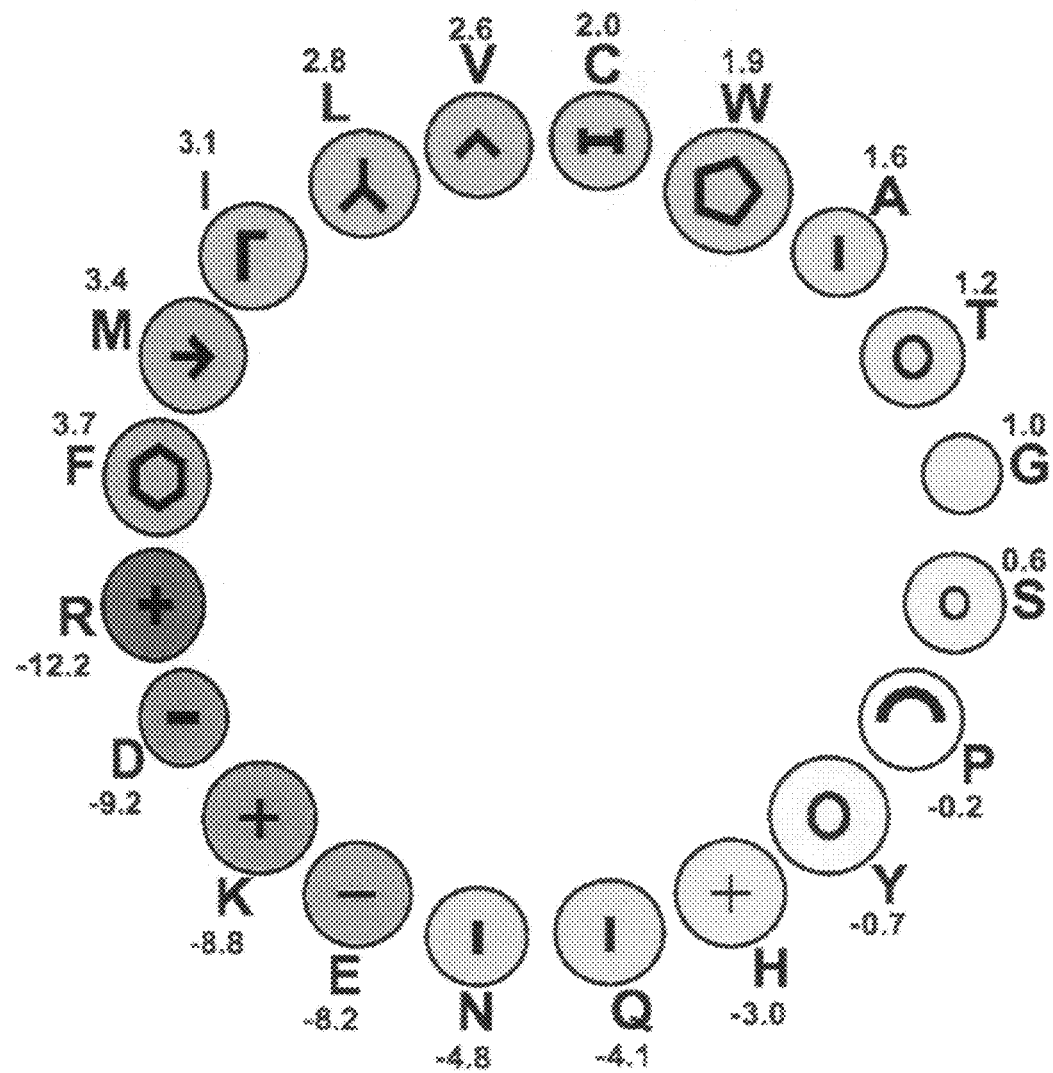
FIG. 3. Molly font wheel presented with single letter codes adjacent to each glyph. The number values are relative hydrophobicities represented by the number of kcal/mole necessary to exteriorize an amino acid in an alpha helix from the inside of a lipid layer.

Lytic Peptide Fragments of the Present Invention

| Name | Sequence | # | MWT | *MWT |
|---|---|---|---|---|
| JC15 | FAKKFAKKFKKFAKKFAKFAFAF (SEQ ID NO: 5) | 23 | 2775.48 | 3388.48 |
| JC15-18N | FAKKFAKKFKKFAKKFAK (SEQ ID NO: 28) | 18 | 2191.79 | 2804.79 |
| JC15-12N | FAKKFAKKFKKF (SEQ ID NO: 8) | 12 | 1517.93 | 1953.93 |
| JC15-15C | KKFKKFAKKFAKFAF (SEQ ID NO: 7) | 15 | 1864.36 | 2359.36 |
| JC15-10C | FAKKFAKFAF (SEQ ID NO: 29) | 10 | 1204.48 | 1463.48 |
| JC15-10N | FAKKFAKKFK (SEQ ID NO: 1) | 10 | 1242.58 | 1619.58 |

TABLE 1-continued

Lytic Peptide Fragments of the Present Invention

| Name | Sequence | # | MWT | *MWT |
|---|---|---|---|---|
| PL-1 | QAWDSQSPHAHGYIPSKFPNKNLKKNY (SEQ ID NO: 22) | 27 | 3156.52 | 3615.52 |
| PL-2 | MFGNGKGYRGKRATTVTGTP (SEQ ID NO: 3) | 20 | 2099.41 | 2417.41 |
| C-1 | IVRRADRAAVPIVNLKDELL (SEQ ID NO: 24) | 20 | 2261.70 | 2648.70 |
| PF-1 | PTAQLIATLKNGRKI (SEQ ID NO: 26) | 15 | 1623.97 | 1882.97 |
| PF-2 | LDLQAPLYKKIIKKLLES (SEQ ID NO: 27) | 18 | 2113.62 | 2477.62 |
| JC41 | FKLRAKIKVRLRAKIKL (SEQ ID NO: 18) | 17 | 2081.72 | 2635.72 |

*MWT indicates the molecular weight after addition of companion ions.

TABLE 2

Data collected from experiments measuring angiogenic activity in semi-quantitative/qualitative scale.

| Treatment | Samples | | | | | | | | Mean | % Diff. |
|---|---|---|---|---|---|---|---|---|---|---|
|  | 1 | 2 | 3 | 4 | 5 | 6 | 7 | 8 |  |  |
| Control | 2 | 3 | 2 | 3 | 2 | 3 |  |  | 2.50 | 0.00 |
| JC15-18N (SEQ ID NO: 28) | 3 | 2 | 3 | 3 |  |  |  |  | 2.75 | 10.00 |
| JC15-15C (SEQ ID NO: 7) | 2 | 3 | 2 | 3 | 2 | 3 | 3 | 4 | 2.75 | 10.00 |
| JC15-12N (SEQ ID NO: 8) | 4 | 2 | 3 | 2 | 3 | 2 | 3 |  | 2.71 | 8.57 |
| JC15 (SEQ ID NO: 5) | 3 | 2 | 3 | 2 | 3 |  |  |  | 2.60 | 4.00 |
| PL-1 (SEQ ID NO: 22) | 2 | 3 | 2 | 3 | 2 | 3 | 2 | 3 | 2.50 | 0.00 |
| PF-2 (SEQ ID NO: 27) | 2 | 3 | 2 | 3 |  |  |  |  | 2.50 | 0.00 |
| PF-1 (SEQ ID NO: 26) | 2 | 3 | 2 | 3 |  |  |  |  | 2.50 | 0.00 |
| JC15-10C (SEQ ID NO: 29) | 2 | 3 | 2 | 3 | 2 | 3 | 2 | 3 | 2.50 | 0.00 |
| PL-2 (SEQ ID NO: 3) | 2 | 3 | 2 | 3 | 2 | 3 | 2 |  | 2.43 | -2.86 |
| JC15-10N (SEQ ID NO: 1) | 1 | 2 | 2 | 3 | 1 | 2 | 2 |  | 1.86 | -25.71 |
| C-1 (SEQ ID NO: 24) | 2 | 2 | 3 | 1 | 2 | 1 |  |  | 1.83 | -26.67 |

TABLE 3 a presentation of the peptides tested in the Matrigel experiment (Example 3) showing hydrophobic amino acids with white rectangles below the sequences and hydrophilic amino acids as dark rectangles below the sequences.

| Peptide | Sequence | Mean | % Diff. |
|---|---|---|---|
| Control | DOES NOT APPLY | 2.50 | 0.00 |
| JC15 (SEQ ID NO: 5) | F A K K F A K K F K K F A K K F A K F A F A F | 2.60 | 4.00 |
| JC15-18N (SEQ ID NO: 28) | F A K K F A K K F K K F A K K F A K | 2.75 | 10.00 |
| JC15-15C (SEQ ID NO: 7) | K K F K K F A K K F A K | 2.75 | 10.00 |
| JC15-10C (SEQ ID NO: 29) | F A K K F A K F A F | 2.50 | 0.00 |
| JC15-12N (SEQ ID NO: 8) | F A K K F A K K F K K F | 2.71 | 8.40 |
| JC15-10N (SEQ ID NO: 1) | F A K K F A K K F K | 1.86 | -25.60 |
| C-1 (SEQ ID NO: 24) | I V R R A D R A A V P I V N L K D E L L | 1.83 | -26.80 |
| PF-2 (SEQ ID NO: 27) | L D L Q A P L Y K K I I K K L L E S | 2.50 | 0.00 |
| PF-1 (SEQ ID NO: 26) | P T A Q L I A T L K N G R K I | 2.50 | 0.00 |
| PL-1 (SEQ ID NO: 22) | Q A W D S Q S P H A G Y I P S K F P N K N L K K N Y | 2.50 | 0.00 |
| PL-2 (SEQ ID NO: 3) | M F G N G K G Y R G K R A T T V T G T P | 2.43 | -2.80 |

TABLE 4

Amino acid sequences of selected domains derived from several cytokines, oncostatin and endostatin.

| SEQ ID NO | DESIGNATION | OLD DESIGNATION | INTERNAL SEQUENCE |
|---|---|---|---|
| 34 | CCL5 | RANTES | WVREYINSLE |
| 32 | CCL8 | MCP-2 | WVRDSMKHL |
| 37 | CCL11 | EOTAXIN | KKWVQDSMK |
| 38 | CCL12 | MCP-5 | WVKNSINHL |
| 39 | CCL13 | MCP-4 | WVQNYMKHL |
| 40 | CCL14 | CC-1/CC-3 | KWVQDYIKDM |
| 33 | CCL15 | MIP-5 | LTKKGRQVCA |
| 42 | CCL16 | — | KRVKNAVKY |
| 43 | CCL18 | MIP-4 | LTKRGRQICA |
| 44 | CCL18 | MIP-4 | KKWVQKYIS |
| 45 | CCL19 | MIP-3 BETA | WVERIIQRLQ |
| 46 | CCL23 | MIP-3 | LTKKGRRFC |
| 47 | CCL27 | ESKINE | LSDKLLRKVI |
| 48 | CCL28 | CCK1 | VSHHISRRLL |
| 49 | XCL2 | SCM-1 BETA | WVRDVVRSMD |
| 50 | CX3CL1 | FRACTALKINE | WVKDAMQHLD |
| 51 | CXCL1 | MGSA | MVKKIIEKM |
| 52 | CXCL3 | MIP-2 BETA | MVQKIIEKIL |
| 53 | CXCL4 | PF-4 | LYKKIIKKLL |
| 54 | CXCL5 | ENA-78 | FLKKVIQKIL |
| 55 | CXCL6 | GCP-2 | FLKKVIQKIL |
| 56 | CXCL7 | PRO-PLATELET PRO | IKKIVQKKLA |
| 57 | CXCL8 | IL8 | WVQRVVEKFL |
| 50 | CXCL11 | IP-9 | IIKKVER |
| 60 | CXCL13 | B13 | WIQRMMEVLR |
| 61 | IL10 | — | AVEQVKNAFN |
| 62 | IL5 | — | TVERLFKNLS |
| 63 | IL7 | — | FLKRLLQEI |
| 64 | IL11 | — | LDRLLRRL |
| 65 | IL20 | — | LLRHLLRL |
| 66 | IL22 | — | KDTVKKLGE |
| 67 | IL24 | — | LFRRAFKQLD |

TABLE 4-continued

Amino acid sequences of selected domains derived from several cytokines, oncostatin and endostatin.

| SEQ ID NO | DESIG-NATION | OLD DESIGNATION | INTERNAL SEQUENCE |
|---|---|---|---|
| 68 | IL26 | — | WIKKLLESSQ |
| 69 | ONCO-frag | — | SRKGKRLM |
| 70 | ENDO-frag | F-COLLAGEN XVIII | IVRRADRAAV |
| 71 | Endostatin | — | Too long for table |

TABLE 5

Chemokines involved in development of various diseases. The sequences of the chemokines are shown in the sequence listing with the following sequence numbers: IL8 (SEQ ID NO: 57), MIG (SEQ ID NO: 31), MCP1 (SEQ ID NO: 32), MIP1a (SEQ ID NO: 33) and Rantes (SEQ ID NO: 34).

| | Chemokine | | | | |
|---|---|---|---|---|---|
| Disease | IL8 | MIG | MCP1 | MIP1a | Rantes |
| Exp Autoimmune Enc | | | | | |
| Multiple Sclerosis | | | | | |
| Allografts | | | | | |
| Asthma | | | | | |
| Rheumatoid Arthritis | | | | | |
| Osteo Arthritis | | | | | |
| Neoplasia | | | | | |
| Vascular Disease | | | | | |

FIG. 1 illustrates the angiogenic process. Blood vessel walls in arteries, arterioles, and capillaries, are lined by basement membrane composed of endothelial cells. Angiogenesis occurs mainly in the capillaries or post-capillary venules. In response to cytokine stimulation, endothelial cells break down the basement membrane, migrate into the extra vascular space, proliferate, and reorganize to form a new vessel. The endothelial cell carries its own internal defense against stray growth factors and it is the most sensitive of all cells to growth control by cell shape. With recent research, it seems that mechanical forces on a cell are necessary for growth factors, cytokines and hormones, to function. These soluble molecules will remain inactive unless they are coupled to the mechanical forces generated by specific insoluble molecules (collagen and fibronectin). These insoluble molecules lie in the extra cellular matrix and bind to specific receptors and integrins on the cell surface. This allows a cell to pull against its extra cellular matrix and to generate tension over the interconnected cytoskeletal linkages. Thus, cell shape changes are a prerequisite for entry of that cell into the cell cycle and subsequent gene expression and cell division. In fact, for the endothelial cell it is not the area and shape configuration of the outer cell membrane that supplies the direct mechano-chemical information that permits DNA synthesis, but rather the shape of the nucleus. Nevertheless, nuclear shape is governed by the shape of the outer cell membrane and by tensile forces transmitted to the nucleus over the cytoskeletal network. When the shape of the nucleus is stretched beyond 60-70 microns there is net DNA synthesis.

The extra cellular matrix appears to contain special components; in particular, certain proteoglycans that bind and store these growth factors making them inaccessible to endothelial cells. For example, it is known that basic fibroblast growth factor (FGF) and vascular endothelial growth factor (VEGF) bind to heparin sulfate proteoglycan. The basement membrane itself may also inhibit endothelial growth. The laminin B1 chain contains two internal sites that, in the form of synthetic peptides having the sequence RGD and YSGR, inhibit angiogenesis. Furthermore, collagen XVIII is localized to the perivascular region of large and small vessels and a 187 amino acid fragment, called endostatin, is a potent and specific inhibitor of endothelial proliferation. Several other endogenous proteins block the multiplication of endothelial cells and exert a reduced angiogenic effect. In each case, the endothelial inhibitor activity is found in a fragment of a larger protein which itself lacks inhibitory activity.

Angiogenesis plays a role in various disease processes. It is well known that angiogenesis is involved in development of malignant tumors and cancer diseases. Moreover, angiogenesis is associated with rheumatoid arthritis. Chronic inflammation may also involve pathological angiogenesis; examples of angiogenesis related inflammation diseases are ulcerative colitis and Crohn's disease. Chronic inflammation has been implicated to be the primary causative factor in several diseases including arthritis, multiple sclerosis, cervical spondylosis, tinnitus, systemic lupus, erythematosis, graft rejection, psoriasis, atherosclerosis, hypertension, and ischemia-reperfusion.

Figure 4:
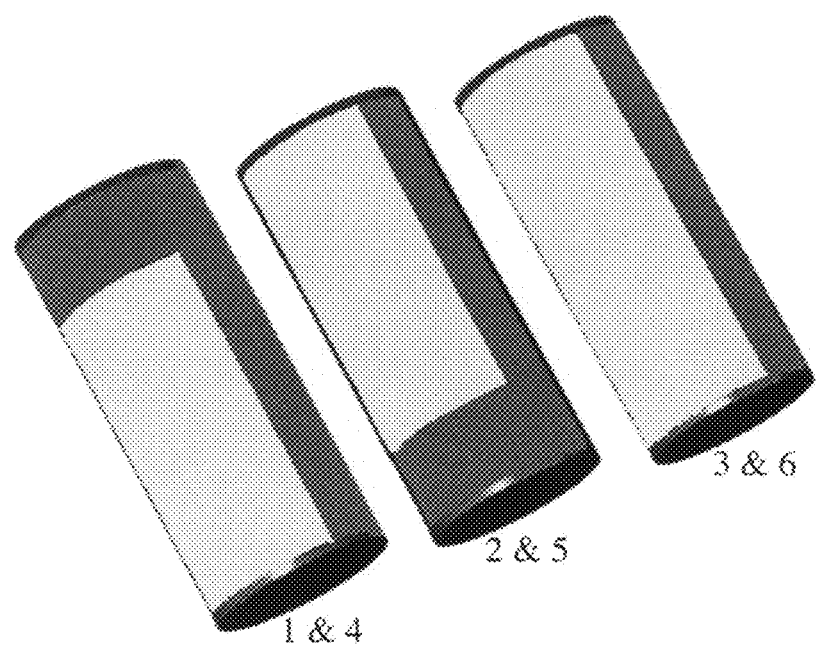
FIG. 4 illustrates three arrangements of naturally occurring peptides. The top band on the cylinders indicates the amino-terminus of the peptide while the gray band represents the carboxy-terminus. Representative examples or natural peptides that fit this classification system are: mellitin-class 1; cecropins-class 2, and magainins-class 3.
Figure 10:
FIG. 10 shows sequence of the fragment C-1 (SEQ ID NO: 24) derived from Human Collagen XVIII.

Lytic peptides are small proteins that are major components of the antimicrobial defense systems of numerous species (AMPs). They are a ubiquitous feature of nearly all multi-cellular and some single-cellular life forms. They generally consist of between 10-40 amino acids in length, which have the potential for forming discrete secondary structures. Often, they exhibit the property of amphipathy. An amphipathic α-helix may be depicted as a cylinder with one curved hemi-cylinder face composed primarily of non-polar amino acids while the other face is composed of polar amino acids Four distinct types of lytic peptides were discovered in the last decade; examples of each type are melittin, cecropins, magainins, and defensins. The properties of naturally occurring peptides suggest at least three distinct alpha-helical classes consisting of different arrangements of amphipathic and hydrophobic regions (FIG. 4). The top band on the cylinders indicates the amino-terminus of the peptide while the gray band represents the carboxy-terminus. The cyan color represents regions that are predominately hydrophobic and the magenta color represent regions that are hydrophilic. Representative examples of natural peptides, which fit this classification system are: melittin-class 1, cecropins-class 2, and magainins-class 3 (note, 99% of all the known natural peptides fall within this classification system, data not shown). Therefore, separate synthetic peptides can be subdivided into distinct classes based on what has been observed in Nature.

Some examples of natural lytic peptides and their sequence as cast in the glyph motif are listed in FIG. 5, along with representative optimized analogs. These are shown in a typical linear array and are read from left to right.

The only natural lytic peptides that assume a b-conformation are the defensins and protegrins. They can assume this shape because of intra-disulfide linkages that lock them into this form, an absolute requisite for activity. We have completely novel classes of peptides that form b-sheets without the necessity of disulfide linkages. An example, JC41 is shown in FIG. 6. The columnar array of hydrophobic and positive charged amino acids is apparent when the peptide adopts an amphipathic b-form. However, the width of the columns is narrower but overall length is greater than a peptide that adopts an amphipathic α-helix conformation.

Anti-Angiogenesis

Lytic peptides are active in eliminating tumor-derived cells by causing direct osmotic lysis. Based on this demonstrable activity, reason suggests that in order to demonstrate in vivo activity the peptide must be injected directly into the tumor. Indeed, that is the case. With just a few injections over a period of several days, tumors are permanently eliminated using the most active anti-tumor peptide, JC15 (SEQ ID NO: 5), yet tested. A follow-up series of experiments was designed to determine what occurs when this peptide is injected in a site removed from the tumor (in other words, can it express any systemic activity)?" The results were unexpected as most of the tumors also disappeared in several animal tumor models. However, in some cases there was little activity. To determine what might be happening in vivo, radiolabeled JC15 (SEQ ID NO: 5) was chemically synthesized with all alanines labeled with either $^3$H or $^{14}$C. Since the labeling pattern was asymmetric, it enabled us to follow the physical state of the peptide once it had been injected into the animal by comparing the unique ratios of $^3$H/$^{14}$C that would result if the peptide experienced proteolysis. It was found that within minutes the labeled peptide was hydrolyzed to fragments of various lengths no matter the route of administration but in the circulation approximately 14% of the radiolabel persisted for at least 24 hours with minimal further degradation (unpublished observations). The possibility emerged that the systemic in vivo anti-cancer activity was retained within specific fragments of JC15 (SEQ ID NO: 5). Based on these results, several peptide fragments were selected for further study as outlined herein below.

DETAILED DESCRIPTION OF THE INVENTION

Selected Peptide Fragments from Full-Length Corresponding Protein

The synthetic peptide fragments of the present invention are listed in Table 1 Fragments PL-1 (SEQ ID NO: 22) and PL-2 (SEQ ID NO: 3) are peptide fragments of plasminogen protein (SEQ ID NO: 20). Fragment C-1 (SEQ ID NO: 2) is a peptide fragment of the larger protein molecule Collagen XVIII (SEQ ID NO: 23) endostatin fragment (SEQ ID NO: 70). The two peptides PF-1 (SEQ ID NO: 26) and PF-2 (SEQ ID NO: 27) are fragments of platelet factor-4. Included are also several fragments of JC15 (SEQ ID NO: 5), JC15-18N (SEQ ID NO: 28), JC15-12N (SEQ ID NO: 8), JC15-15C (SEQ ID NO: 7), JC15-10C (SEQ ID NO: 29), JC15-10N (SEQ ID NO: 1), The peptide fragments of the present invention were prepared by the method F-moc peptide synthesis procedure that is a typical method for the preparation of peptide sequences.

Procedure for Determining Angiogenic Activity of Peptide Fragments (Either Acceleration or Inhibition)

Figure 13:
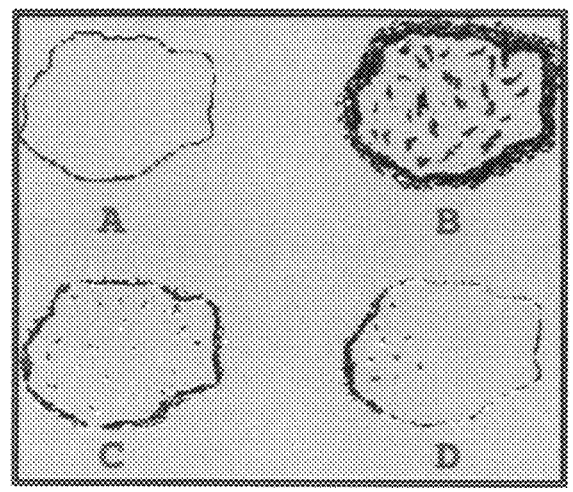
FIG. 13 illustrates Matrigel gels. A shows how a section of a Matrigel gel deposit looks like under the microscope soon after surgical implantation. The sample in B is derived from the control at the conclusion of the experiment. Intense activity is present with numerous cells attaching to the surface of the Matrigel. Cells begin to penetrate the deposit and organize into discrete structures that coalesce to form the beginning of tubes twisting and branching every way. In C, a typical sample from the peptide C-1 (SEQ ID NO: 24) treatment is shown. This treatment caused far fewer cellular associations evident at the perimeter of the Matrigel deposit. Consequently, there were far fewer cells and cellular structures inside of the Matrigel. Only one peptide fragment from JC15, JC15-10N, possessed anti-angiogenic activity. A representative section of a Matrigel deposit from this set of animals is shown in D.

Matrigel deposits were surgically implanted on both sides of 4 mice per treatment yielding a possible 8 samples per treatment. Matrigel is a polymeric substance that appears to be relatively inert in animals and it can serve as a matrix that allows experimentation in vivo on many different difficult-to-study-processes. Prior to implantation, the Matrigel was allowed to imbibe fibroblast growth factor 1 (FGF1). This protein is a powerful inducer of angiogenesis and its presence guarantees that sufficient activity will be observed within the allotted time period of the experiment. Therefore, any inhibition of angiogenesis is likely to be a real phenomenon as the experiment has been set to heavily favor the angiogenic process. Angiogenesis occurs by day 14 and beginning Day 1 (Day 0=day of implantation), mice were injected IP daily with 20 μg of peptide in 100 μl of normal saline. The animals were sacrificed on Day 14, and each Matrigel deposit divided longitudinally and fixed in 10% buffered formalin. One of the halves of each Matrigel deposit was then sectioned. Read-out for this experiment was via histology, with semi-quantitative/qualitative counting of migration of cells and their subsequent assembly of lumenal structures within the Matrigel. This method allows us to observe the full physiologic spectrum of effects, and was useful in delineating trends. FIG. 13 shows the summary rendition of what, on average was observed. In FIG. 13, A represents what a section of a Matrigel gel deposit looks like under the microscope soon after surgical implantation. The sample in B is derived from the control at the conclusion of the experiment. Intense activity is present with numerous cells attaching to the surface of the Matrigel. Cells begin to penetrate the deposit and organize into discrete structures that coalesce to form the beginning of tubes twisting and branching in many directions. These venules eventually connect with the system carrying blood and it is possible to see red cells and lymphocytes within them. This process is called "arborization", derived from the fact that the angiogenic process most closely resembles the growth of roots and branches of trees. All but two of the peptide treatments looked, more or less, like B (all the peptides of Table 1 were tested). In C, a typical sample from the peptide C-1 (SEQ ID NO: 24) treatment is shown. This treatment caused far fewer cellular associations evident at the perimeter of the Matrigel deposit. Consequently, there were far fewer cells and cellular structures inside of the Matrigel. Only one peptide fragment from JC15 (SEQ ID NO: 5), JC15-10N (SEQ ID NO: 1), possessed anti-angiogenic activity. A representative section of a Matrigel deposit from this set of animals can be found in D. Importantly and surprisingly, not the numbers of internal cells and structures within the Matrigel deposit were reduced, but there was a seeming asymmetry of their organization where activity was evident. There were large regions of Matrigel that had no visibly associated structures and few single cells, including on the periphery, while other regions had some limited activity. This experiment demonstrates that portions of endostatin (SEQ ID NO: 71) and JC15 (SEQ ID NO: 5) possess significant anti-angiogenic activity.

Table 2 shows the data collected from the experiment using semi-quantitative/qualitative scale for measuring angiogenic activity. This method is used as an initial assessment to find compounds that possess angiogenic activity, molecules that either accelerate or inhibit the process. This system ranks each sample using a 0 to 4 plus (+) scale. Thus, B in FIG. 13 would yield a score of +++ while no + sign would yield a value of 0, as in A in FIG. 13. In Table 3 the data is modified to a numerical form and plotted averages are shown.

Analysis shows that significant differences exist between the JC15-10N (SEQ ID NO: 1) & C-1 (SEQ ID NO: 24) pair, from the rest of the treatments. However, JC15-10N (SEQ ID NO: 1) and C-1 (SEQ ID NO: 24) are not significantly different from one another.

Figure 14:
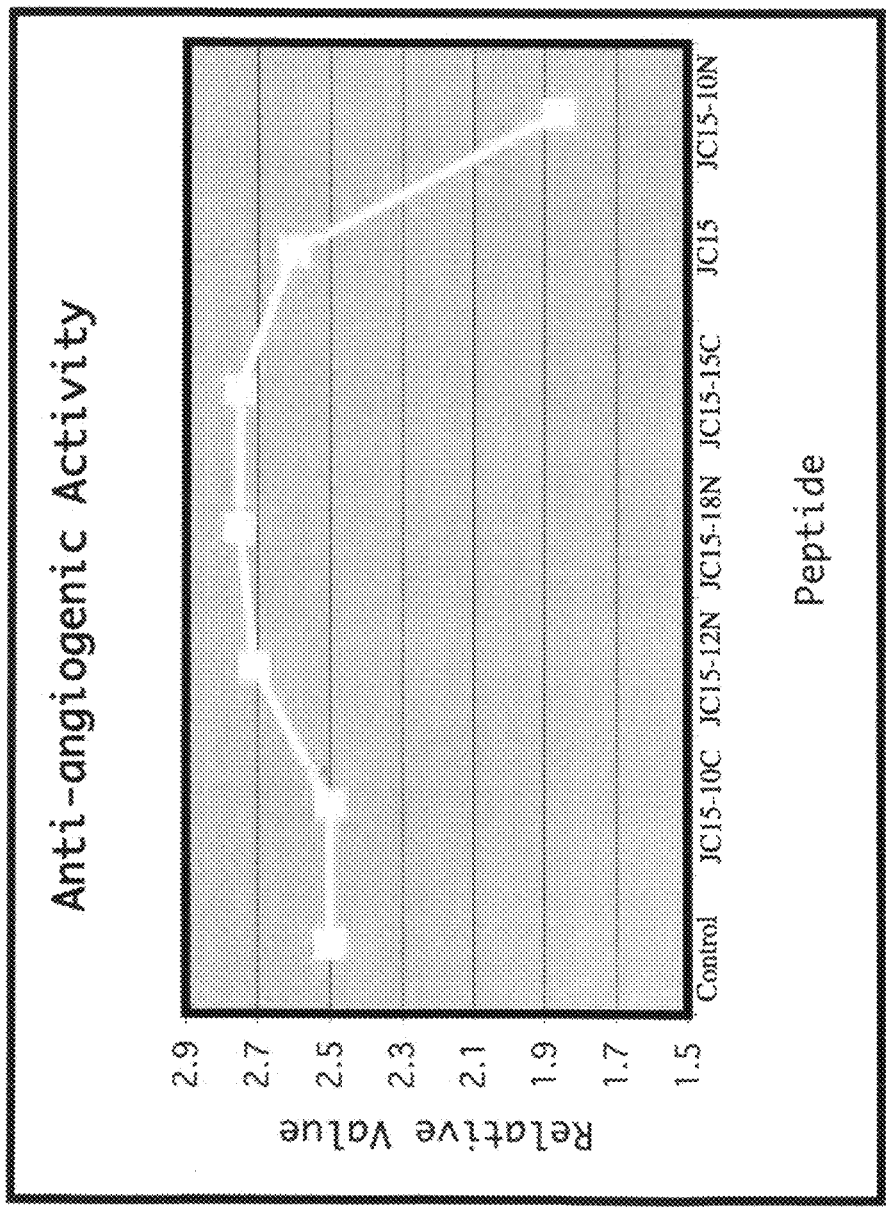
FIG. 14 shows anti-angiogenic activity of peptides of different lengths. As compared to control level the highest anti-angiogenic activity was obtained by peptides having less than 12 amino acids and centered on the amino terminal end.

Based upon these data. It would appear that several of the peptides may actually promote angiogenesis. For example, mice treated with JC15-18N (SEQ ID NO: 28), JC15-15C (SEQ ID NO: 7), and JC15-12N (SEQ ID NO: 8), all show levels of activity higher than the control. Indeed, Matrigel deposits treated with the latter two peptides had the only top level (++++) scores of the entire experiment. ✓-amphipathic peptides of high positive charge density can cause cell proliferation, with the effect being more pronounced in peptides below 18 amino acids in length. These smaller peptides' lytic activity is greatly reduced because they are simply too short to physically span the membrane, the site of their direct mode of action. It is interesting that the level of activity is closer to the control in the full-length JC15 (SEQ ID NO: 5) treatment group as opposed to some of its smaller fragments. A peak of angiogenic activity above the control is seen when the peptide is between 12 and 18 amino acids in length, culminating in observable anti-angiogenic activity when the peptide is shorter than 12 amino acids (FIG. 14).

Example 6

Structure/Function Relationships of the Peptides and their Anti-Angiogenesis Effect Table 3 allows one to see similarities or differences in the presence or absence of charged amino acids and their position with respect to hydrophobic (white rectangles) and other hydrophilic amino acids (dark rectangles) in the peptides tested in the Matrigel experiment.

One can see structural similarities, within sequence motifs, when sequences are presented as in Table 3. Of course, all of the fragments of JC15 (SEQ ID NO: 5) are going to be identical to different regions of the full-length JC15 (SEQ ID NO: 5) molecule. However, it is also apparent that the endostatin fragment, C-1 (SEQ ID NO: 24), has more than just a passing resemblance to JC15 and its fragments, as do portions of the peptides from plasminogen. In addition, the C-terminal half of PF-2 (SEQ ID NO: 3), derived from platelet factor 4, shares similarly significant structural homology.

Figure 15:
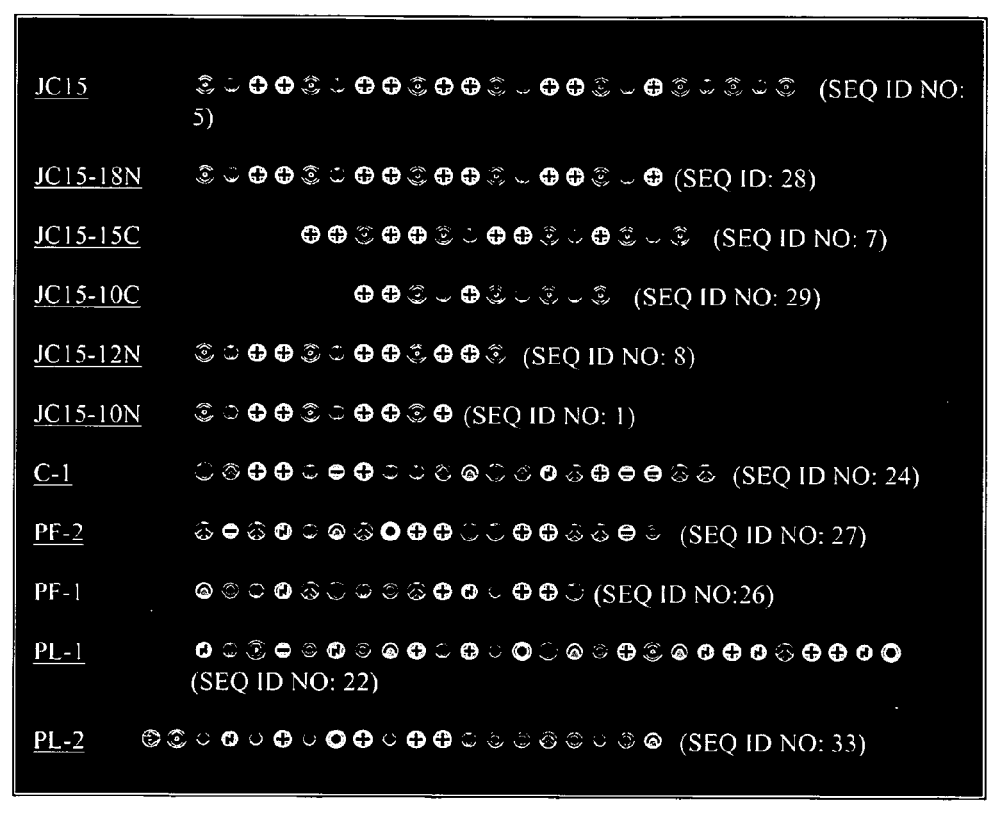
Figure 18:
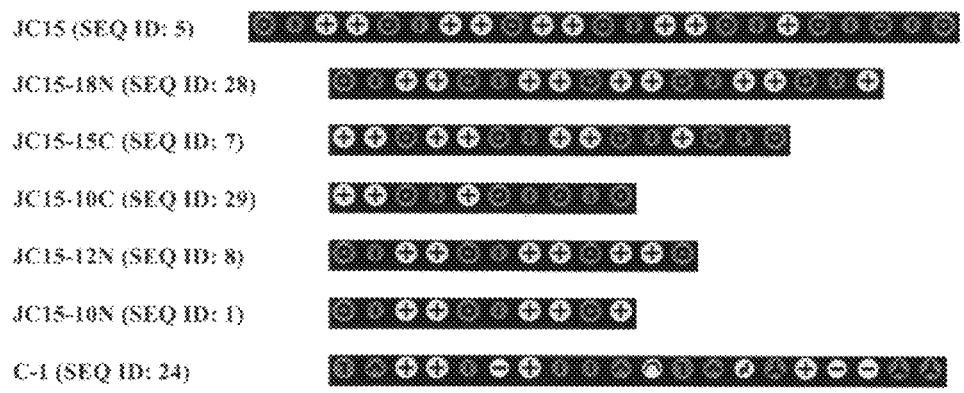
FIG. 18. Comparison of an endostatin fragment with full-length D2A21 peptide and its generated fragments

As can be seen from FIGS. 15 and 18, there is a close physico-chemical relatedness of C1 (SEQ ID NO: 24) and JC1510N (SEQ ID NO: 1) when illustrated with Molly.

These structurally homologous regions are enough alike to all modulate angiogenesis in some way. Most biochemical processes occur at the surfaces of different macromolecules that associate or bind to specific regions on one another within a discrete three-dimensional space. These binding sequences are often rather short stretches of a protein, say, 4 to 8 amino acids. It is entirely within the realm of possibility that there are only 5 or so amino acids that comprise the critical binding region that interacts specifically with target macromolecules initiating an in vivo anti-angiogenic response. The data support the hypothesis that C-1 (SEQ ID NO: 24) and JC15-10N (SEQ ID NO: 1) possess this binding region.

Figure 16:
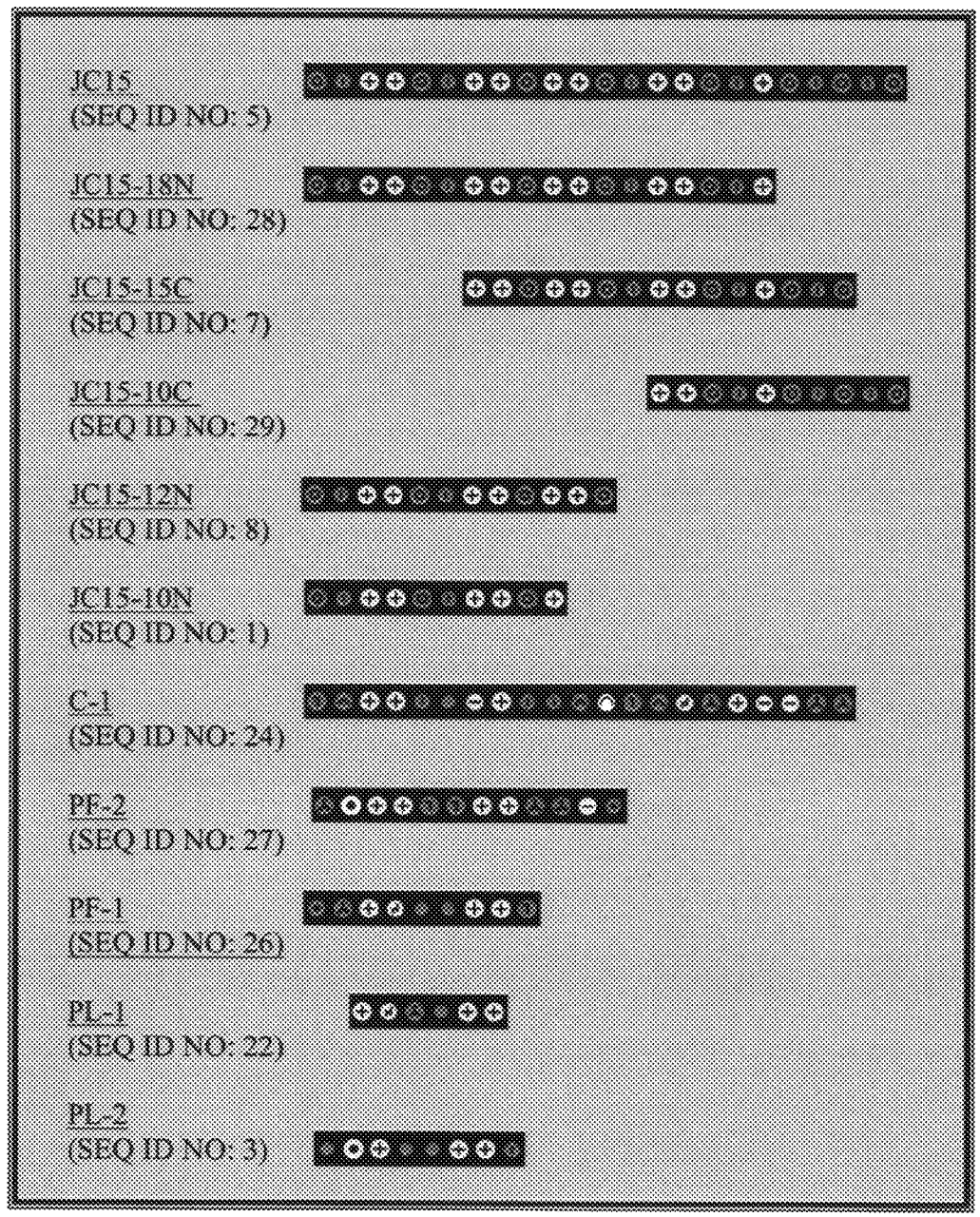
FIG. 16 illustrates the common motif of peptides of Example 6.

In FIG. 15 the sequences are cast in Molly and FIG. 16 is a simple schematic illustration derived from FIG. 15. By keeping in mind that each hydrophilic square is, with just a few exceptions, a "+" charged amino acid, the following conclusions can be made:

JC15 (SEQ ID NO: 5) and all of its fragments possess the same type of internal sequence of 7 or 9 amino acids, with JC15 (SEQ ID NO: 5) and JC15-18N (SEQ ID NO: 28) retaining one of each. Noting the shift of one amino acid, most importantly, the same can be said for the peptides C-1 (SEQ ID NO: 24), *PF-1 (SEQ ID NO: 26), and *PF-2 (SEQ ID NO: 27).

The anti-angiogenic fragment must be of a certain length. Even if a fragment retains the putative 7 or 9 amino acid binding sequence, like JC15 (SEQ ID NO: 5), JC15-18N (SEQ ID NO: 28), JC15-15C (SEQ ID NO: 7), and JC15-12N (SEQ ID NO: 8), it still cannot exert an anti-angiogenic effect. Clearly, the simplest explanation is that these sequences cannot "fit" into the target-binding site. How critical this size requirement is, can be borne out by the fact that a fragment identical to JC15-10N (SEQ ID NO: 1), but with the addition of two amino acids, JC15-12N (SEQ ID NO: 8), does not inhibit angiogenesis. In fact, it may actually cause an opposite effect. Then, one may ask, why does C-1 (SEQ ID NO: 24) possess anti-angiogenic activity when it seems to violate the size requirement, after all, it is 21 amino acids in length? My best guess, at this time, is that the proline, with just 2 amino acids separating it from the putative binding sequence, directs the rest of the fragment away from the target-binding site, reducing interference to a minimum. After all, that is proline's function—to allow bends and turns in proteins. Alternatively, it could be processed in the animal to a shorter fragment.

More than a specific length is necessary. JC15-10C (SEQ ID NO: 29) and JC15-10N (SEQ ID NO: 1) are the same size yet JC15-10N (SEQ ID NO: 1) is the only one that possesses anti-angiogenic activity. Even though JC15-10C (SEQ ID NO: 29) contains a probable 7 amino acid binding sequence, the addition of 3 hydrophobic amino acids on the C-terminal end of JC15-10C (SEQ ID NO: 29) are enough to negate binding, 2 of the 3 being bulky phenylalanines. In addition, one can conclude that a more optimal binding fragment contains several pairs of charged or other hydrophilic amino acids in the binding sequence see JC15-10N (SEQ ID NO: 1) and C-1 (SEQ ID NO: 24). Perhaps, another reason why JC15-10C (SEQ ID NO: 29) was inactive.

The "interchangeability" of like amino acids is most apparent in comparison of JC15-10N (SEQ ID NO: 1) with C-1 (SEQ ID NO: 29). Even though their sequences are quite different, almost perfect correspondence is observed when they are cast in the molecular font. It is possible that JC15-10N (SEQ ID NO: 1) could be made even more active by removing one of the internal hydrophobic amino acids and reducing its length by one or two amino acids from its C-terminal end. Also, the addition of a negatively charged amino acid, within the charged pair, may be desirable.

Example 7

Chemokine Anatomy and the Design of Novel Domains to Delineate Specific Cellular Activities Chronic inflammation has been implicated to be the primary causative factor in various diseases including: arthritis, multiple sclerosis, cervical spondylosis, tinnitus, systemic lupus, erythematosis, graft rejection, psoriasis, atherosclerosis, hypertension, and ischemia-reperfusion. The surprising fact is that just a handful of pro-inflammatory chemokines are responsible and according to this disclosure JC15-10N (SEQ ID NO: 1) has structural analogies within the sequences of each molecule.

While there are more than 50 chemokines that have been characterized, but a clearly smaller set is involved in diseases. Table 4 provides internal sequence of a number of chemokines and Table 5 shows the chemokines involved in several diseases.

Figure 19B:
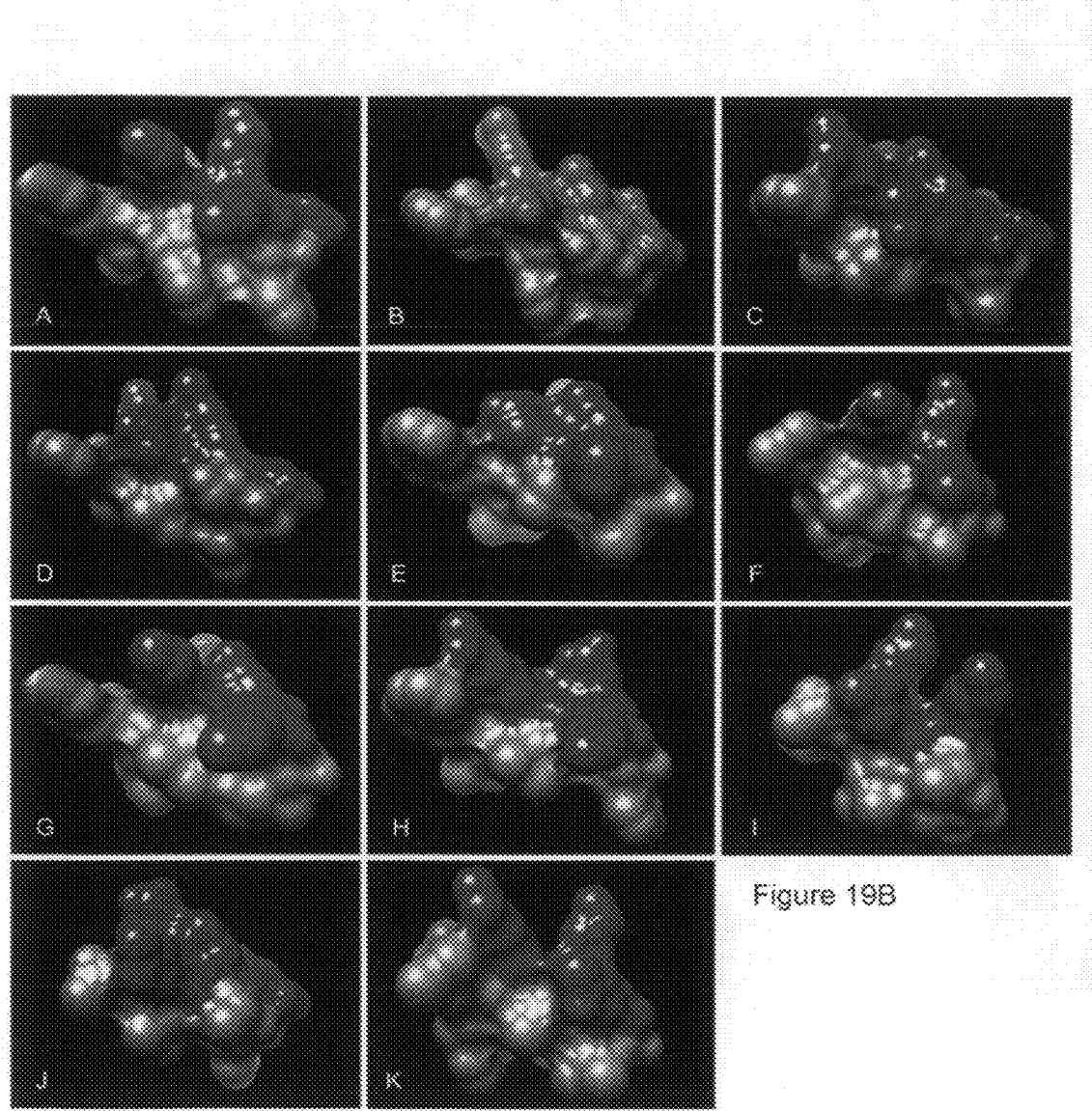
FIG. 19B displays the three-dimensional representations of the peptide fragments obtained using the UCSF Chimera software.

The chemical/structural similarities of the chemokines in FIG. 19 A with JC15-10N (SEQ ID NO: 1) are easy to recognize. They conserve amphipathy and charge density to a high degree and their 3-dimensional structure (FIG. 19B) would be quite similar to JC15-10N (SEQ ID NO: 1. Mostly they all appear after a proline and are more often than not at the C-terminus—this yields distinct I would predict that all of the above sequences would possess anti-angiogenic and anti-inflammatory activity much like JC15-10N. Thus, these key sequences of each domain, within the specific protein, no doubt functions as a down-regulator or off/brake switch for the inflammatory process.

Example 8

Antiangiogenic and Anti-Inflammatory Effects of JC15-10N as Tested in a Lion Infected with FIV Nasty is a male lion in North Carolina Zoological Park. He was diagnosed to suffer Feline Immunodeficiency virus FIV. FIV attacks the immune system of cats, much like the human immunodeficiency virus (HIV) attacks the immune system of human beings. FIV infects many cell types in its host, including CD4+ and CD8+T lymphocytes, B lymphocytes, and macrophages. FIV eventually leads to debilitation of the immune system in its feline hosts by the infection and exhaustion of T-helper (CD4+) cells.

Figure 20:
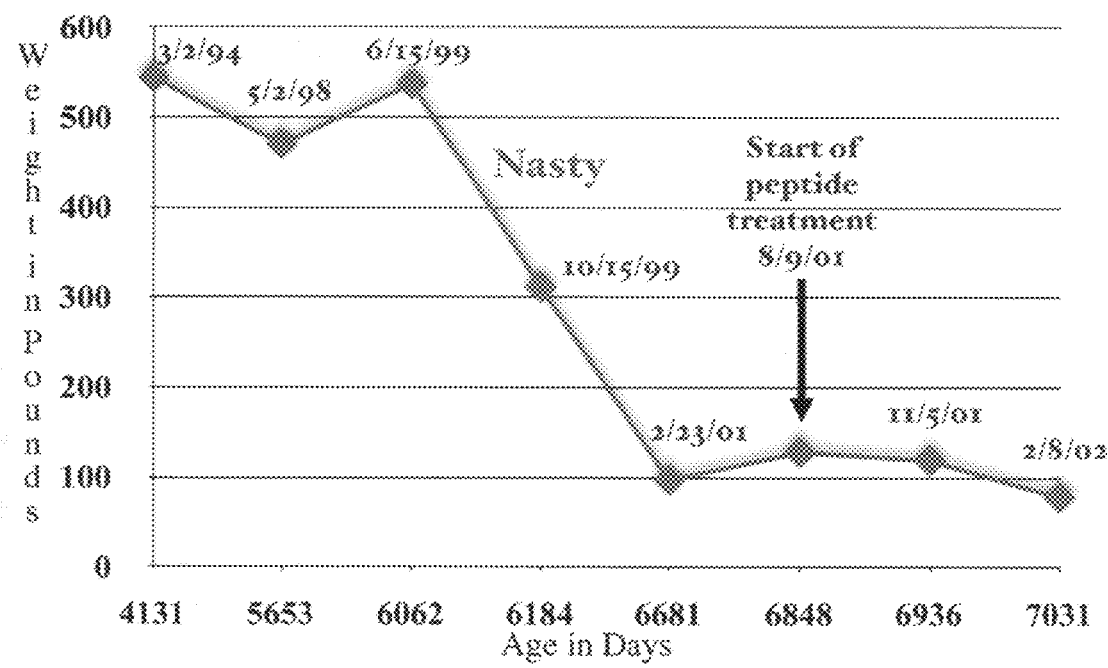
FIG. 20. Changes in the absolute CD4+ Cell Counts in the sera of Nasty the lion before and after peptide treatment.
Figure 21:
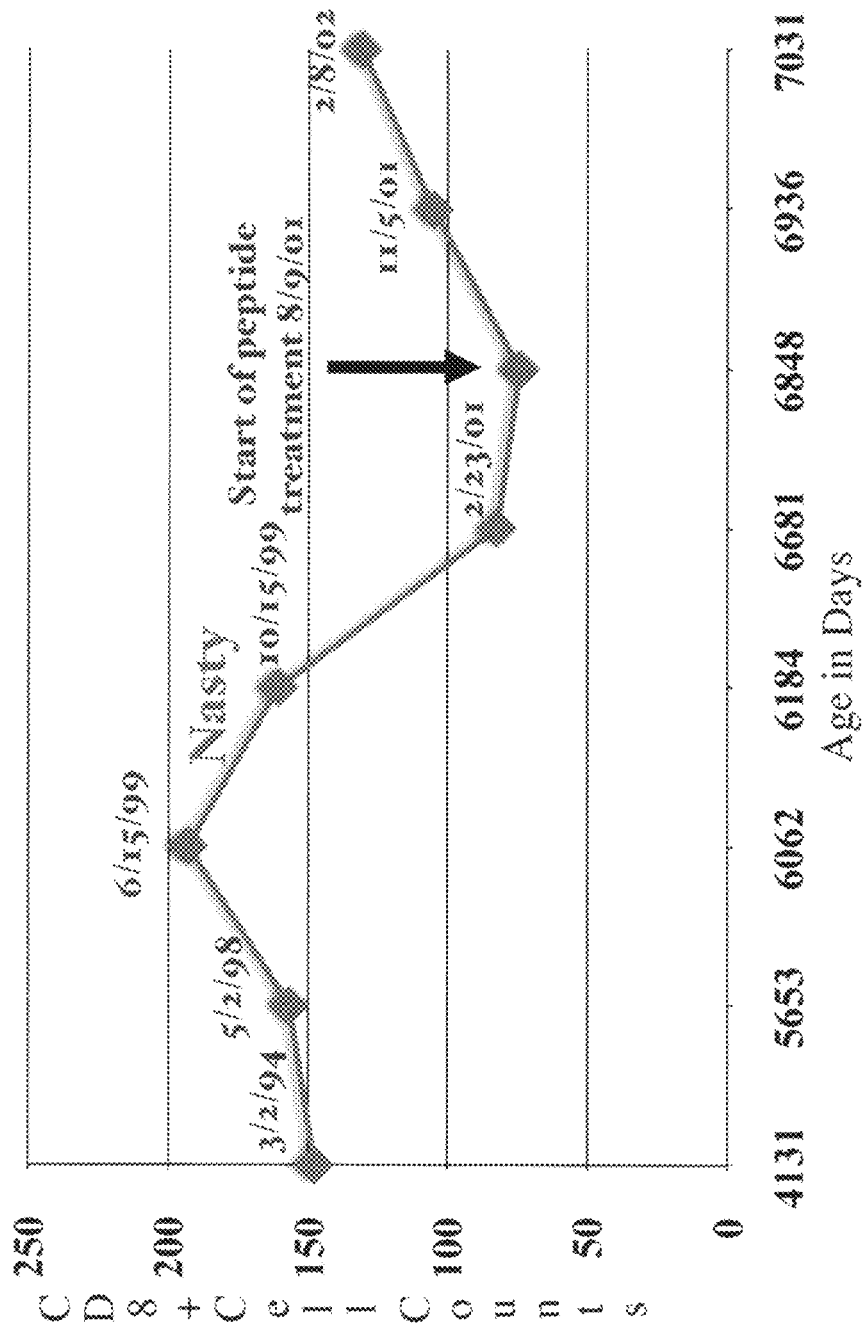
FIG. 21 Changes in the absolute CD8+ Cell Counts in the sera of Nasty the lion before and after peptide treatment.

Nasty was treated weekly with 70 mg I.M injections of JC15-10N. FIG. 20 shows changes in the absolute CD4+ Cell Counts of Nasty before and after peptide treatment. It can be seen that starting of peptide treatment stabilized the CD4+ cell counts. FIG. 21 shows changes in the absolute CD8+ cell counts of Nasty before and after peptide treatment. Starting of the treatment prevented the decrease and actually, the cell counts began to rise soon after the Example 9

Treatment of Arthritis with JC15-10N (SEQ ID NO: 1) Peptide

Figure 22:
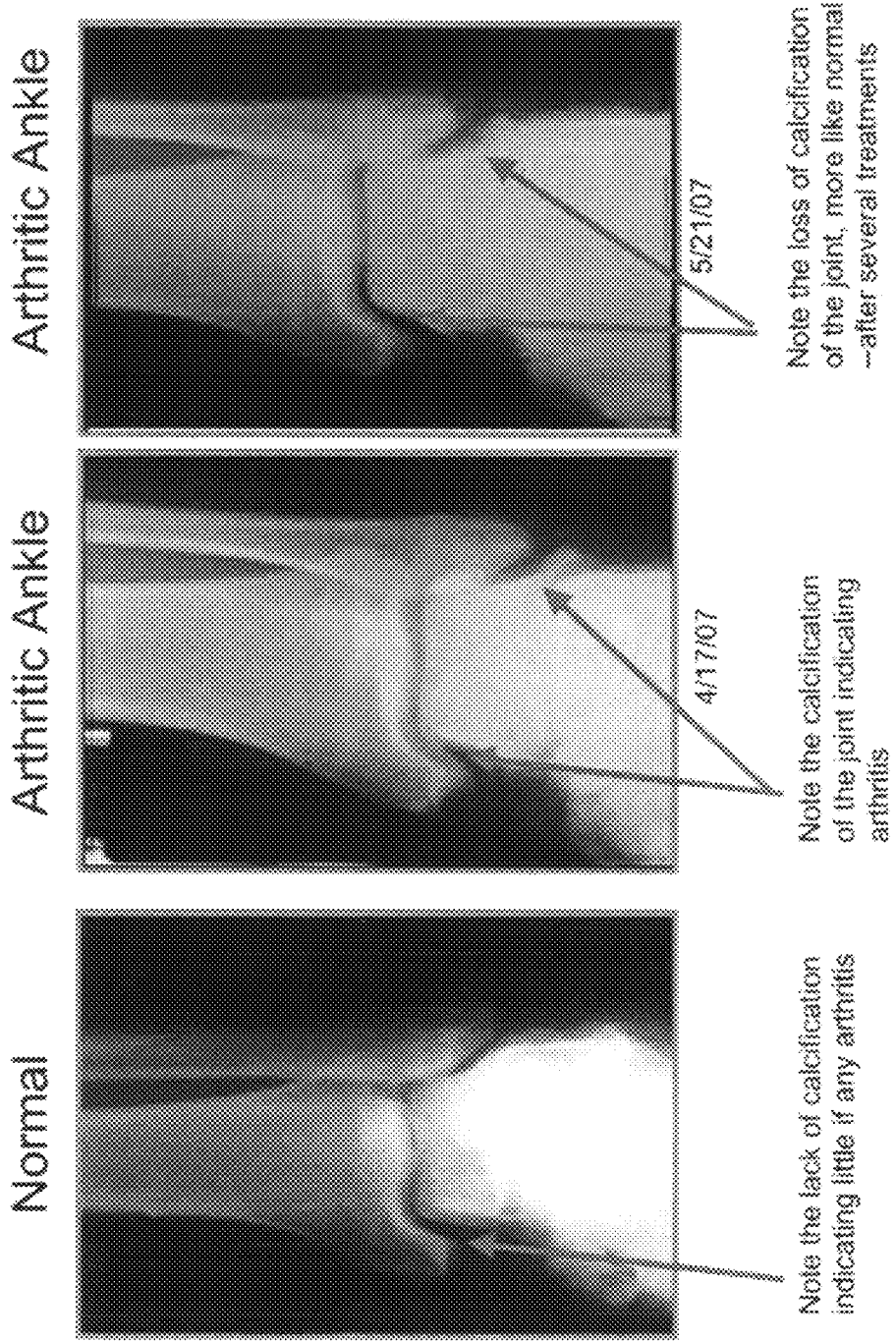
FIG. 22 shows X-ray figures of a normal ankle, an arthritic ankle and an arthritic ankle after several peptide treatments (10 mg subcutaneous injections once a week for one month and then one injection per month for maintenance).

A patient with arthritis was treated by subcutaneous injection of 10 mg once a week for one month and then once a month for maintenance doses. A visible indication of arthritis is calcification of joints. The calcification of the ankle joints disappeared during this time indicated in the x-ray results are shown in FIG. 22

The invention claimed is:

1. A lytic peptide fragment consisting of the amino acid sequence of FAKKFAKKFK (SEQ ID NO: 1), wherein the lytic peptide fragment inhibits angiogenesis.

2. A pharmaceutical composition comprising a lytic peptide fragment consisting of the amino acid sequence of FAKKFAKKFK (SEQ ID NO: 1) or a pharmaceutically acceptable salt thereof.

3. A lytic peptide fragment consisting of the amino acid sequence selected from the group consisting of FAKKFAKKFKKFAKFAFAF (SEQ ID NO: 4), FAKKFAKKFAKKFAK (SEQ ID NO: 6), KKFKKFAKKFAKFAF (SEQ ID NO: 7) and FAKKFAKKFKKF (SEQ ID NO: 8) or a pharmaceutically acceptable salt thereof, wherein the lytic peptide fragment angiogenesis.

4. A pharmaceutical composition comprising a lytic peptide fragment consisting of the amino acid sequence selected from the group consisting of FAKKFAKKFKKFAKFAFAF (SEQ ID NO: 4), FAKKFAKKFAKKFAK (SEQ ID NO: 6), KKFKKFAKKFAKFAF (SEQ ID NO: 7) and FAKKFAKKFKKF (SEQ ID NO: 8) or a pharmaceutically acceptable salt thereof.

* * * * *

```
                      SEQUENCE LISTING

<160> NUMBER OF SEQ ID NOS: 70

<210> SEQ ID NO 1
<211> LENGTH: 10
<212> TYPE: PRT
<213> ORGANISM: Artificial Sequence
<220> FEATURE:
<223> OTHER INFORMATION: Completely Synthesized

<400> SEQUENCE: 1

Phe Ala Lys Lys Phe Ala Lys Lys Phe Lys
1               5                   10

<210> SEQ ID NO 2
<211> LENGTH: 20
<212> TYPE: PRT
<213> ORGANISM: Homo sapiens
<220> FEATURE:
<223> OTHER INFORMATION: Endostatin Fragment-20

<400> SEQUENCE: 2

Ile Val Arg Arg Ala Asp Arg Ala Ala Val Pro Ile Val Asn Leu Lys
1               5                   10                  15

Asp Glu Leu Leu
            20

<210> SEQ ID NO 3
<211> LENGTH: 20
<212> TYPE: PRT
<213> ORGANISM: Homo sapiens
<220> FEATURE:
<223> OTHER INFORMATION: PL-2

<400> SEQUENCE: 3

Met Phe Gly Asn Gly Lys Gly Tyr Arg Gly Lys Arg Ala Thr Thr Val
1               5                   10                  15

Thr Gly Thr Pro
```

```
<210> SEQ ID NO 4
<211> LENGTH: 19
<212> TYPE: PRT
<213> ORGANISM: Artificial Sequence
<220> FEATURE:
<223> OTHER INFORMATION: Completely Synthesized

<400> SEQUENCE: 4

Phe Ala Lys Lys Phe Ala Lys Lys Phe Lys Lys Phe Ala Lys Phe Ala
1               5                   10                  15

Phe Ala Phe

<210> SEQ ID NO 5
<211> LENGTH: 23
<212> TYPE: PRT
<213> ORGANISM: Artificial Sequence
<220> FEATURE:
<223> OTHER INFORMATION: Completely Synthesized

<400> SEQUENCE: 5

Phe Ala Lys Lys Phe Ala Lys Lys Phe Lys Lys Phe Ala Lys Lys Phe
1               5                   10                  15

Ala Lys Phe Ala Phe Ala Phe
            20

<210> SEQ ID NO 6
<211> LENGTH: 15
<212> TYPE: PRT
<213> ORGANISM: Artificial Sequence
<220> FEATURE:
<223> OTHER INFORMATION: Completely Synthesized

<400> SEQUENCE: 6

Phe Ala Lys Lys Phe Ala Lys Lys Phe Ala Lys Lys Phe Ala Lys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Completely Synthesized

<400> SEQUENCE: 7

Lys Lys Phe Lys Lys Phe Ala Lys Lys Phe Ala Lys Phe Ala Phe
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: Completely Synthesized

<400> SEQUENCE: 8

Phe Ala Lys Lys Phe Ala Lys Lys Phe Lys Lys Phe
1               5                   10

<210> SEQ ID NO 9
<211> LENGTH: 26
<212> TYPE: PRT
<213> ORGANISM: Apis melifera
<220> FEATURE:
<223> OTHER INFORMATION: Melittin
```

<400> SEQUENCE: 9

Gly Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25

<210> SEQ ID NO 10
<211> LENGTH: 25
<212> TYPE: PRT
<213> ORGANISM: Rana pipens
<220> FEATURE:
<223> OTHER INFORMATION: Pipinin

<400> SEQUENCE: 10

Phe Leu Pro Ile Ile Ala Gly Val Ala Ala Lys Val Leu Phe Pro Lys
1               5                   10                  15

Ile Phe Cys Ala Ile Ser Lys Lys Cys
                20                  25

<210> SEQ ID NO 11
<211> LENGTH: 33
<212> TYPE: PRT
<213> ORGANISM: Homo sapiens
<220> FEATURE:
<223> OTHER INFORMATION: Adenoregulin

<400> SEQUENCE: 11

Gly Leu Trp Ser Lys Ile Lys Glu Val Gly Lys Glu Ala Ala Lys Ala
1               5                   10                  15

Ala Ala Lys Ala Ala Gly Lys Ala Ala Leu Gly Ala Val Ser Glu Ala
                20                  25                  30

Val

<210> SEQ ID NO 12
<211> LENGTH: 35
<212> TYPE: PRT
<213> ORGANISM: Hyalophora cecropia
<220> FEATURE:
<223> OTHER INFORMATION: Cecropin B

<400> SEQUENCE: 12

Lys Trp Lys Ile Phe Lys Lys Ile Glu Lys Val Gly Arg Asn Ile Arg
1               5                   10                  15

Asn Gly Ile Ile Lys Ala Gly Pro Ala Val Ala Val Leu Gly Glu Ala
                20                  25                  30

Lys Ala Leu
        35

<210> SEQ ID NO 13
<211> LENGTH: 34
<212> TYPE: PRT
<213> ORGANISM: Homo sapiens
<220> FEATURE:
<223> OTHER INFORMATION: Andropin

<400> SEQUENCE: 13

Val Phe Ile Asp Ile Leu Asp Lys Val Glu Asn Ala Ile His Asn Ala
1               5                   10                  15

Ala Gln Val Gly Ile Gly Phe Ala Lys Pro Phe Glu Lys Leu Ile Asn
                20                  25                  30

Pro Lys

<210> SEQ ID NO 14
<211> LENGTH: 23
<212> TYPE: PRT
<213> ORGANISM: Xenopus laevis
<220> FEATURE:
<223> OTHER INFORMATION: Magainin II

<400> SEQUENCE: 14

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 15
<211> LENGTH: 23
<212> TYPE: PRT
<213> ORGANISM: Artificial Sequence
<220> FEATURE:
<223> OTHER INFORMATION: Completely Synthesized

<400> SEQUENCE: 15

Phe Ala Phe Ala Phe Lys Ala Phe Lys Lys Ala Phe Lys Lys Phe Lys
1               5                   10                  15

Lys Ala Phe Lys Lys Ala Phe
            20

<210> SEQ ID NO 16
<211> LENGTH: 23
<212> TYPE: PRT
<213> ORGANISM: Artificial Sequence
<220> FEATURE:
<223> OTHER INFORMATION: Completely Synthesized

<400> SEQUENCE: 16

Phe Val Lys Lys Val Ala Lys Lys Ala Lys Lys Val Ala Lys Lys Ala
1               5                   10                  15

Val Lys Val Ala Lys Lys Val
            20

<210> SEQ ID NO 17
<211> LENGTH: 38
<212> TYPE: PRT
<213> ORGANISM: Homo sapiens
<220> FEATURE:
<223> OTHER INFORMATION: beta defensin 1

<400> SEQUENCE: 17

Asp Phe Ala Ser Cys His Thr Asn Gly Gly Ile Cys Leu Pro Asn Arg
1               5                   10                  15

Cys Pro Gly His Met Ile Gln Ile Gly Ile Cys Phe Arg Pro Arg Val
            20                  25                  30

Lys Cys Cys Arg Ser Trp
        35

<210> SEQ ID NO 18
<211> LENGTH: 17
<212> TYPE: PRT
<213> ORGANISM: Artificial Sequence
<220> FEATURE:
<223> OTHER INFORMATION: Completely Synthesized

<400> SEQUENCE: 18

Phe Lys Leu Arg Ala Lys Ile Lys Val Arg Leu Arg Ala Lys Ile Lys

-continued

```
1               5                   10                  15
Leu

<210> SEQ ID NO 19
<211> LENGTH: 18
<212> TYPE: PRT
<213> ORGANISM: Homo sapiens
<220> FEATURE:
<223> OTHER INFORMATION: Protegrin

<400> SEQUENCE: 19

Arg Gly Gly Arg Leu Cys Tyr Cys Arg Arg Phe Cys Val Cys Val
1               5                   10                  15

Gly Arg

<210> SEQ ID NO 20
<211> LENGTH: 810
<212> TYPE: PRT
<213> ORGANISM: Homo sapiens
<220> FEATURE:
<223> OTHER INFORMATION: Plasminogen

<400> SEQUENCE: 20

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Pro Ser Ser Gly Pro Thr
            260                 265                 270
```

-continued

```
Tyr Gln Cys Leu Lys Gly Thr Gly Glu Asn Tyr Arg Gly Asn Val Ala
            275                 280                 285

Val Thr Val Ser Gly His Thr Cys Gln His Trp Ser Ala Gln Thr Pro
290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
            325                 330                 335

Thr Thr Asn Ser Gln Val Arg Trp Glu Tyr Cys Lys Ile Pro Ser Cys
                340                 345                 350

Asp Ser Ser Pro Val Ser Thr Glu Gln Leu Ala Pro Thr Ala Pro Pro
            355                 360                 365

Glu Leu Thr Pro Val Val Gln Asp Cys Tyr His Gly Asp Gly Gln Ser
        370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
            485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
            530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
            565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
        610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
            645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
            675                 680                 685
```

```
Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 21
<211> LENGTH: 256
<212> TYPE: PRT
<213> ORGANISM: Homo sapiens
<220> FEATURE:
<223> OTHER INFORMATION: Angiostatin

<400> SEQUENCE: 21

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240
```

```
Thr Thr Asn Ser Gln Val Arg Trp Glu Tyr Cys Lys Ile Pro Ser Cys
                245                 250                 255
```

<210> SEQ ID NO 22
<211> LENGTH: 27
<212> TYPE: PRT
<213> ORGANISM: Homo sapiens
<220> FEATURE:
<223> OTHER INFORMATION: PL-1

<400> SEQUENCE: 22

```
Gln Ala Trp Asp Ser Gln Ser Pro His Ala His Gly Tyr Ile Pro Ser
1               5                   10                  15

Lys Phe Pro Asn Lys Asn Leu Lys Lys Asn Tyr
            20                  25
```

<210> SEQ ID NO 23
<211> LENGTH: 684
<212> TYPE: PRT
<213> ORGANISM: Homo sapiens
<220> FEATURE:
<223> OTHER INFORMATION: Collagen Fragment

<400> SEQUENCE: 23

```
Gly Glu Val Gly Ala Asp Gly Ile Pro Gly Phe Pro Gly Leu Pro Gly
1               5                   10                  15

Arg Glu Gly Ile Ala Gly Pro Gln Gly Pro Lys Gly Asp Arg Gly Ser
            20                  25                  30

Arg Gly Glu Lys Gly Asp Pro Gly Lys Asp Gly Leu Gly Gln Pro Gly
        35                  40                  45

Leu Pro Gly Pro Arg Gly Pro Pro Gly Pro Val Val Tyr Val Ser Glu
    50                  55                  60

Gln Asp Gly Ser Val Leu Ser Val Pro Gly Pro Glu Gly Arg Arg Gly
65                  70                  75                  80

Phe Ala Gly Phe Pro Gly Pro Ala Gly Pro Lys Gly Asn Leu Gly Ser
                85                  90                  95

Lys Gly Glu Leu Gly Ser Pro Gly Pro Lys Gly Glu Lys Gly Glu Pro
            100                 105                 110

Gly Ser Ile Phe Ser Pro Asp Gly Gly Ala Leu Gly Pro Ala Gln Lys
        115                 120                 125

Gly Ala Lys Gly Glu Pro Gly Phe Arg Gly Pro Pro Gly Leu Tyr Gly
    130                 135                 140

Arg Pro Gly Tyr Lys Gly Glu Ile Gly Phe Pro Gly Arg Pro Gly Arg
145                 150                 155                 160

Pro Gly Met Asn Gly Leu Lys Gly Glu Lys Gly Glu Pro Gly Asp Ala
                165                 170                 175

Gly Leu Gly Phe Gly Met Arg Gly Met Pro Gly Pro Gly Pro Pro Pro
            180                 185                 190

Gly Pro Pro Gly Pro Pro Gly Pro Gly Leu Pro Gly Asn Gln Gly
        195                 200                 205

Pro Pro Gly Pro Lys Gly Pro Lys Gly Glu Val Gly Pro Pro Gly Pro
    210                 215                 220

Pro Gly Gln Phe Pro Phe Asp Phe Leu Gln Lys Glu Ala Glu Met Lys
225                 230                 235                 240

Gly Glu Lys Gly Asp Arg Gly Asp Ala Gly Gln Lys Gly Glu Arg Gly
                245                 250                 255

Glu Pro Gly Gly Gly Gly Glu Phe Gly Ser Ser Leu Pro Gly Ala Pro
            260                 265                 270
```

-continued

```
Gly Ala Pro Gly Pro Arg Gly Tyr Pro Gly Ile Pro Gly Pro Lys Gly
            275                 280                 285

Gly Ala Pro Gly Pro Arg Gly Tyr Pro Gly Ile Pro Gly Pro Lys Gly
            290                 295                 300

Glu Ser Ile Arg Gly Gln Pro Gly Pro Gly Pro Gln Gly Pro Pro
305                 310                 315                 320

Gly Ile Gly Tyr Glu Gly Arg Gln Gly Pro Gly Pro Gly Pro
                325                 330                 335

Pro Gly Pro Pro Ser Phe Pro Gly Pro His Arg Gln Thr Ile Ser Val
            340                 345                 350

Pro Gly Pro Pro Ser Phe Pro Gly Pro His Arg Gln Thr Ile Ser Val
            355                 360                 365

Gly Ala Ser Ser Gly Gln Val Arg Leu Trp Ala Thr Arg Gln Ala Met
            370                 375                 380

Leu Gly Gln Val His Glu Val Pro Glu Gly Trp Leu Ile Phe Val Ala
385                 390                 395                 400

Glu Gln Glu Glu Leu Tyr Val Arg Val Gln Asn Gly Phe Arg Lys Val
                405                 410                 415

Gln Leu Glu Ala Arg Thr Pro Leu Pro Arg Gly Thr Asp Asn Glu Val
            420                 425                 430

Ala Ala Leu Gln Pro Pro Val Val Gln Leu His Asp Ser Asn Pro Tyr
            435                 440                 445

Pro Arg Arg Glu His Pro His Pro Thr Ala Arg Pro Trp Arg Ala Asp
450                 455                 460

Asp Ile Leu Ala Ser Pro Gly Leu Pro Glu Pro Gln Pro Tyr Pro
465                 470                 475                 480

Gly Gly Pro His His Ser Ser Tyr Val His Cys Gly Pro Ala Arg Pro
                485                 490                 495

Thr Ser Pro Pro Ala His Ser His Arg Asp Phe Gln Pro Val Leu His
            500                 505                 510

Leu Val Ala Leu Asn Ser Pro Leu Ser Gly Gly Met Arg Gly Ile Arg
            515                 520                 525

Gly Ala Asp Phe Gln Cys Phe Gln Gln Ala Arg Ala Val Gly Leu Ala
            530                 535                 540

Gly Thr Phe Arg Ala Phe Leu Ser Ser Arg Leu Gln Asp Leu Tyr Ser
545                 550                 555                 560

Ile Val Arg Arg Ala Asp Arg Ala Ala Val Pro Ile Val Asn Leu Lys
                565                 570                 575

Asp Glu Leu Leu Phe Pro Ser Trp Glu Ala Leu Phe Ser Gly Ser Glu
            580                 585                 590

Gly Pro Leu Lys Pro Gly Ala Arg Ile Phe Ser Phe Asp Gly Lys Asp
            595                 600                 605

Val Leu Arg His Pro Thr Trp Pro Gln Lys Ser Val Trp His Gly Ser
610                 615                 620

Asp Pro Asn Gly Arg Arg Leu Thr Glu Ser Tyr Cys Glu Thr Trp Arg
625                 630                 635                 640

Thr Glu Ala Pro Ser Ala Thr Gly Gln Ala Ser Ser Leu Leu Gly Gly
                645                 650                 655

Arg Leu Leu Gly Gln Ser Ala Ala Ser Cys His His Ala Tyr Ile Val
            660                 665                 670

Leu Cys Ile Glu Asn Ser Phe Met Thr Ala Ser Lys
            675                 680
```

<210> SEQ ID NO 24
<211> LENGTH: 21
<212> TYPE: PRT
<213> ORGANISM: Homo sapiens
<220> FEATURE:
<223> OTHER INFORMATION: C-1

<400> SEQUENCE: 24

Ile Val Arg Arg Ala Asp Arg Ala Ala Val Pro Ile Val Asn Leu Lys
1               5                   10                  15

Asp Glu Leu Leu Phe
            20

<210> SEQ ID NO 25
<211> LENGTH: 70
<212> TYPE: PRT
<213> ORGANISM: Homo sapiens
<220> FEATURE:
<223> OTHER INFORMATION: Platelet Factor 4

<400> SEQUENCE: 25

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser
65                  70

<210> SEQ ID NO 26
<211> LENGTH: 15
<212> TYPE: PRT
<213> ORGANISM: Homo sapiens
<220> FEATURE:
<223> OTHER INFORMATION: Platelet Factor 4 Fragment 1

<400> SEQUENCE: 26

Pro Thr Ala Gln Leu Ile Ala Thr Leu Lys Asn Gly Arg Lys Ile
1               5                   10                  15

<210> SEQ ID NO 27
<211> LENGTH: 18
<212> TYPE: PRT
<213> ORGANISM: Homo sapiens
<220> FEATURE:
<223> OTHER INFORMATION: Platelet Factor 4 Fragment 2

<400> SEQUENCE: 27

Leu Asp Leu Gln Ala Pro Leu Tyr Lys Lys Ile Ile Lys Lys Leu Leu
1               5                   10                  15

Glu Ser

<210> SEQ ID NO 28
<211> LENGTH: 18
<212> TYPE: PRT
<213> ORGANISM: Artificial Sequence
<220> FEATURE:
<223> OTHER INFORMATION: Completely Synthesized

<400> SEQUENCE: 28

```
Phe Ala Lys Lys Phe Ala Lys Lys Phe Lys Phe Ala Lys Lys Phe
1               5                   10                  15

Ala Lys

<210> SEQ ID NO 29
<211> LENGTH: 10
<212> TYPE: PRT
<213> ORGANISM: Artificial Sequence
<220> FEATURE:
<223> OTHER INFORMATION: Completely Synthesized

<400> SEQUENCE: 29

Phe Ala Lys Lys Phe Ala Lys Phe Ala Phe
1               5                   10

<210> SEQ ID NO 30
<211> LENGTH: 99
<212> TYPE: PRT
<213> ORGANISM: Homo sapiens
<220> FEATURE:
<223> OTHER INFORMATION: IL8

<400> SEQUENCE: 30

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser

<210> SEQ ID NO 31
<211> LENGTH: 125
<212> TYPE: PRT
<213> ORGANISM: Homo sapiens
<220> FEATURE:
<223> OTHER INFORMATION: MIG

<400> SEQUENCE: 31

Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Val Leu Lys
                100                 105                 110
```

Val Arg Lys Ser Gln Arg Ser Gln Lys Lys Thr Thr
            115                 120                 125

<210> SEQ ID NO 32
<211> LENGTH: 99
<212> TYPE: PRT
<213> ORGANISM: Homo sapiens
<220> FEATURE:
<223> OTHER INFORMATION: MCP-1

<400> SEQUENCE: 32

Met Lys Val Ser Ala Ala Leu Leu Cys Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 33
<211> LENGTH: 92
<212> TYPE: PRT
<213> ORGANISM: Homo sapiens
<220> FEATURE:
<223> OTHER INFORMATION: MIP-1 alpha 2

<400> SEQUENCE: 33

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
                20                  25                  30

Cys Cys Phe Ser Tyr Thr Ser Arg Gln Ile Pro Gln Asn Phe Ile Ala
            35                  40                  45

Asp Tyr Phe Glu Thr Ser Ser Gln Cys Ser Lys Pro Gly Val Ile Phe
        50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90

<210> SEQ ID NO 34
<211> LENGTH: 91
<212> TYPE: PRT
<213> ORGANISM: Homo sapiens
<220> FEATURE:
<223> OTHER INFORMATION: RANTES

<400> SEQUENCE: 34

Met Lys Val Ser Ala Ala Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

-continued

```
Glu Tyr Phe Tyr Thr Ser Gly Lys Cys Ser Asn Pro Ala Val Val Phe
        50                  55                  60

Val Thr Arg Lys Asn Arg Gln Val Cys Ala Asn Pro Glu Lys Lys Trp
 65                  70                  75                  80

Val Arg Glu Tyr Ile Asn Ser Leu Glu Met Ser
                 85                  90

<210> SEQ ID NO 35
<211> LENGTH: 10
<212> TYPE: PRT
<213> ORGANISM: Homo sapiens
<220> FEATURE:
<223> OTHER INFORMATION: RANTES Fragment

<400> SEQUENCE: 35

Trp Val Arg Glu Tyr Ile Asn Ser Leu Glu
 1               5                  10

<210> SEQ ID NO 36
<211> LENGTH: 9
<212> TYPE: PRT
<213> ORGANISM: Homo sapiens
<220> FEATURE:
<223> OTHER INFORMATION: CCL8 Fragment

<400> SEQUENCE: 36

Trp Val Arg Asp Ser Met Lys His Leu
 1               5

<210> SEQ ID NO 37
<211> LENGTH: 9
<212> TYPE: PRT
<213> ORGANISM: Homo sapiens
<220> FEATURE:
<223> OTHER INFORMATION: CDS

<400> SEQUENCE: 37

Lys Lys Trp Val Gln Asp Ser Met Lys
 1               5

<210> SEQ ID NO 38
<211> LENGTH: 9
<212> TYPE: PRT
<213> ORGANISM: Homo sapiens
<220> FEATURE:
<223> OTHER INFORMATION: CC12 Fragment

<400> SEQUENCE: 38

Trp Val Lys Asn Ser Ile Asn His Leu
 1               5

<210> SEQ ID NO 39
<211> LENGTH: 9
<212> TYPE: PRT
<213> ORGANISM: Homo sapiens
<220> FEATURE:
<223> OTHER INFORMATION: CCL13 Fragment

<400> SEQUENCE: 39

Trp Val Gln Asn Tyr Met Lys His Leu
 1               5

<210> SEQ ID NO 40
<211> LENGTH: 10
<212> TYPE: PRT
```

```
<213> ORGANISM: Homo sapiens
<220> FEATURE:
<223> OTHER INFORMATION: CCL14 Fragment

<400> SEQUENCE: 40

Lys Trp Val Gln Asp Tyr Ile Lys Asp Met
1               5                   10

<210> SEQ ID NO 41
<211> LENGTH: 10
<212> TYPE: PRT
<213> ORGANISM: Homo sapiens
<220> FEATURE:
<223> OTHER INFORMATION: CCL15 Fragment

<400> SEQUENCE: 41

Leu Thr Lys Lys Gly Arg Gln Val Cys Ala
1               5                   10

<210> SEQ ID NO 42
<211> LENGTH: 9
<212> TYPE: PRT
<213> ORGANISM: Homo sapiens
<220> FEATURE:
<223> OTHER INFORMATION: CCL16 Fragment

<400> SEQUENCE: 42

Lys Arg Val Lys Asn Ala Val Lys Tyr
1               5

<210> SEQ ID NO 43
<211> LENGTH: 10
<212> TYPE: PRT
<213> ORGANISM: Homo sapiens
<220> FEATURE:
<223> OTHER INFORMATION: CCL18 Fragment 1

<400> SEQUENCE: 43

Leu Thr Lys Arg Gly Arg Gln Ile Cys Ala
1               5                   10

<210> SEQ ID NO 44
<211> LENGTH: 9
<212> TYPE: PRT
<213> ORGANISM: Homo sapiens
<220> FEATURE:
<223> OTHER INFORMATION: CCL18 Fragment 2

<400> SEQUENCE: 44

Lys Lys Trp Val Gln Lys Tyr Ile Ser
1               5

<210> SEQ ID NO 45
<211> LENGTH: 10
<212> TYPE: PRT
<213> ORGANISM: Homo sapiens
<220> FEATURE:
<223> OTHER INFORMATION: CCL19 Fragment

<400> SEQUENCE: 45

Trp Val Glu Arg Ile Ile Gln Arg Leu Gln
1               5                   10

<210> SEQ ID NO 46
<211> LENGTH: 9
<212> TYPE: PRT
<213> ORGANISM: Homo sapiens
```

```
<220> FEATURE:
<223> OTHER INFORMATION: CCL23 Fragment

<400> SEQUENCE: 46

Leu Thr Lys Lys Gly Arg Arg Phe Cys
1               5

<210> SEQ ID NO 47
<211> LENGTH: 10
<212> TYPE: PRT
<213> ORGANISM: Homo sapiens
<220> FEATURE:
<223> OTHER INFORMATION: CCL27 Fragment

<400> SEQUENCE: 47

Leu Ser Asp Lys Leu Leu Arg Lys Val Ile
1               5                   10

<210> SEQ ID NO 48
<211> LENGTH: 10
<212> TYPE: PRT
<213> ORGANISM: Homo sapiens
<220> FEATURE:
<223> OTHER INFORMATION: CCL28 Fragment

<400> SEQUENCE: 48

Val Ser His His Ile Ser Arg Arg Leu Leu
1               5                   10

<210> SEQ ID NO 49
<211> LENGTH: 10
<212> TYPE: PRT
<213> ORGANISM: Homo sapiens
<220> FEATURE:
<223> OTHER INFORMATION: XCL2 Fragment

<400> SEQUENCE: 49

Trp Val Arg Asp Val Val Arg Ser Met Asp
1               5                   10

<210> SEQ ID NO 50
<211> LENGTH: 10
<212> TYPE: PRT
<213> ORGANISM: Homo sapiens
<220> FEATURE:
<223> OTHER INFORMATION: CX3CL1 Fragment

<400> SEQUENCE: 50

Trp Val Lys Asp Ala Met Gln His Leu Asp
1               5                   10

<210> SEQ ID NO 51
<211> LENGTH: 9
<212> TYPE: PRT
<213> ORGANISM: Homo sapiens
<220> FEATURE:
<223> OTHER INFORMATION: CXCL1 Fragment

<400> SEQUENCE: 51

Met Val Lys Lys Ile Ile Glu Lys Met
1               5

<210> SEQ ID NO 52
<211> LENGTH: 10
<212> TYPE: PRT
<213> ORGANISM: Homo sapiens
<220> FEATURE:
```

<223> OTHER INFORMATION: CXCL3 Fragment

<400> SEQUENCE: 52

Met Val Gln Lys Ile Ile Glu Lys Ile Leu
1               5                   10

<210> SEQ ID NO 53
<211> LENGTH: 10
<212> TYPE: PRT
<213> ORGANISM: Homo sapiens
<220> FEATURE:
<223> OTHER INFORMATION: CXCL4 Fragment

<400> SEQUENCE: 53

Leu Tyr Lys Lys Ile Ile Lys Lys Leu Leu
1               5                   10

<210> SEQ ID NO 54
<211> LENGTH: 10
<212> TYPE: PRT
<213> ORGANISM: Homo sapiens
<220> FEATURE:
<223> OTHER INFORMATION: CXCL5 Fragment

<400> SEQUENCE: 54

Phe Leu Lys Lys Val Ile Gln Lys Ile Leu
1               5                   10

<210> SEQ ID NO 55
<211> LENGTH: 10
<212> TYPE: PRT
<213> ORGANISM: Homo sapiens
<220> FEATURE:
<223> OTHER INFORMATION: CXCL6 Fragment

<400> SEQUENCE: 55

Phe Leu Lys Lys Val Ile Gln Lys Ile Leu
1               5                   10

<210> SEQ ID NO 56
<211> LENGTH: 10
<212> TYPE: PRT
<213> ORGANISM: Homo sapiens
<220> FEATURE:
<223> OTHER INFORMATION: CXCL7 Fragment

<400> SEQUENCE: 56

Ile Lys Lys Ile Val Gln Lys Lys Leu Ala
1               5                   10

<210> SEQ ID NO 57
<211> LENGTH: 10
<212> TYPE: PRT
<213> ORGANISM: Homo sapiens
<220> FEATURE:
<223> OTHER INFORMATION: CXCL8 Fragment

<400> SEQUENCE: 57

Trp Val Gln Arg Val Val Glu Lys Phe Leu
1               5                   10

<210> SEQ ID NO 58
<211> LENGTH: 10
<212> TYPE: PRT
<213> ORGANISM: Homo sapiens
<220> FEATURE:
<223> OTHER INFORMATION: CXCL10 Fragment

```
<400> SEQUENCE: 58

Ala Ile Lys Asn Leu Leu Lys Ala Val Ser
1               5                   10

<210> SEQ ID NO 59
<211> LENGTH: 10
<212> TYPE: PRT
<213> ORGANISM: Homo sapiens
<220> FEATURE:
<223> OTHER INFORMATION: CXCL13 Fragment

<400> SEQUENCE: 59

Trp Ile Gln Arg Met Met Glu Val Leu Arg
1               5                   10

<210> SEQ ID NO 60
<211> LENGTH: 10
<212> TYPE: PRT
<213> ORGANISM: Homo sapiens
<220> FEATURE:
<223> OTHER INFORMATION: IL10 Fragment

<400> SEQUENCE: 60

Ala Val Glu Gln Val Lys Asn Ala Phe Asn
1               5                   10

<210> SEQ ID NO 61
<211> LENGTH: 10
<212> TYPE: PRT
<213> ORGANISM: Homo sapiens
<220> FEATURE:
<223> OTHER INFORMATION: IL5 Fragment

<400> SEQUENCE: 61

Thr Val Glu Arg Leu Phe Lys Asn Leu Ser
1               5                   10

<210> SEQ ID NO 62
<211> LENGTH: 9
<212> TYPE: PRT
<213> ORGANISM: Homo sapiens
<220> FEATURE:
<223> OTHER INFORMATION: IL7 Fragment

<400> SEQUENCE: 62

Phe Leu Lys Arg Leu Leu Gln Glu Ile
1               5

<210> SEQ ID NO 63
<211> LENGTH: 8
<212> TYPE: PRT
<213> ORGANISM: Homo sapiens
<220> FEATURE:
<223> OTHER INFORMATION: XCL2 Fragment

<400> SEQUENCE: 63

Leu Asp Arg Leu Leu Arg Arg Leu
1               5

<210> SEQ ID NO 64
<211> LENGTH: 8
<212> TYPE: PRT
<213> ORGANISM: Homo sapiens
<220> FEATURE:
<223> OTHER INFORMATION: IL20 Fragment
```

```
<400> SEQUENCE: 64

Leu Leu Arg His Leu Leu Arg Leu
1               5

<210> SEQ ID NO 65
<211> LENGTH: 9
<212> TYPE: PRT
<213> ORGANISM: Homo sapiens
<220> FEATURE:
<223> OTHER INFORMATION: IL22 Fragment

<400> SEQUENCE: 65

Lys Asp Thr Val Lys Lys Leu Gly Glu
1               5

<210> SEQ ID NO 66
<211> LENGTH: 10
<212> TYPE: PRT
<213> ORGANISM: Homo sapiens
<220> FEATURE:
<223> OTHER INFORMATION: IL24 Fragment

<400> SEQUENCE: 66

Leu Phe Arg Arg Ala Phe Lys Gln Leu Asp
1               5                   10

<210> SEQ ID NO 67
<211> LENGTH: 10
<212> TYPE: PRT
<213> ORGANISM: Homo sapiens
<220> FEATURE:
<223> OTHER INFORMATION: IL26 Fragment

<400> SEQUENCE: 67

Trp Ile Lys Lys Leu Leu Glu Ser Ser Gln
1               5                   10

<210> SEQ ID NO 68
<211> LENGTH: 8
<212> TYPE: PRT
<213> ORGANISM: Homo sapiens
<220> FEATURE:
<223> OTHER INFORMATION: Oncostatin Fragment

<400> SEQUENCE: 68

Ser Arg Lys Gly Lys Arg Leu Met
1               5

<210> SEQ ID NO 69
<211> LENGTH: 10
<212> TYPE: PRT
<213> ORGANISM: Homo sapiens
<220> FEATURE:
<223> OTHER INFORMATION: Endostatin Fragment

<400> SEQUENCE: 69

Ile Val Arg Arg Ala Asp Arg Ala Ala Val
1               5                   10

<210> SEQ ID NO 70
<211> LENGTH: 183
<212> TYPE: PRT
<213> ORGANISM: Homo sapiens
<220> FEATURE:
<223> OTHER INFORMATION: Endostatin

<400> SEQUENCE: 70
```

```
His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20              25                  30

Cys Phe Gln Gln Ala Arg Ala Val Gly Leu Ala Gly Thr Phe Arg Ala
        35              40                  45

Phe Leu Ser Ser Arg Leu Gln Asp Leu Tyr Ser Ile Val Arg Arg Ala
        50              55                  60

Asp Arg Ala Ala Val Pro Ile Val Asn Leu Lys Asp Glu Leu Leu Phe
65                  70              75                      80

Pro Ser Trp Glu Ala Leu Phe Ser Gly Ser Glu Gly Pro Leu Lys Pro
                85              90                  95

Gly Ala Arg Ile Phe Ser Phe Asp Gly Lys Asp Val Leu Arg His Pro
            100             105                 110

Thr Trp Pro Gln Lys Ser Val Trp His Gly Ser Asp Pro Asn Gly Arg
        115             120                 125

Arg Leu Thr Glu Ser Tyr Cys Glu Thr Trp Arg Thr Glu Ala Pro Ser
    130             135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
            165             170                 175

Ser Phe Met Thr Ala Ser Lys
            180
```